(12) United States Patent
Scheffler et al.

(10) Patent No.: US 10,154,694 B2
(45) Date of Patent: Dec. 18, 2018

(54) SENSOR GARMENT

(71) Applicant: adidas AG, Herzogenaurach (DE)

(72) Inventors: Kim Scheffler, Glen Mills, PA (US); Melanie M. Maslany, Philadelphia, PA (US)

(73) Assignee: adidas AG, Herzogenaurach (DE)

( * ) Notice: Subject to any disclaimer, the term of this patent is extended or adjusted under 35 U.S.C. 154(b) by 1170 days.

(21) Appl. No.: 14/444,613

(22) Filed: Jul. 28, 2014

(65) Prior Publication Data
US 2015/0067943 A1 Mar. 12, 2015

Related U.S. Application Data

(63) Continuation of application No. 13/077,520, filed on Mar. 31, 2011, now Pat. No. 8,818,478.

(51) Int. Cl.
*A61B 5/00* (2006.01)
*A41D 13/12* (2006.01)
(Continued)

(52) U.S. Cl.
CPC ............. *A41D 1/002* (2013.01); *A41D 1/005* (2013.01); *A41D 13/0007* (2013.01); *A41D 13/1281* (2013.01); *A61B 5/0002* (2013.01); *A61B 5/0205* (2013.01); *A61B 5/6802* (2013.01); *A61B 5/6805* (2013.01);
(Continued)

(58) Field of Classification Search
CPC ... A61B 5/6802; A61B 5/6804–5/6806; A61B 2562/22–2562/228; A41D 1/002; A41D 13/0007; A41D 13/1281; A41D 1/005
See application file for complete search history.

(56) References Cited

U.S. PATENT DOCUMENTS 3,307,546 A 3/1967 Cherio et al.
3,534,727 A 10/1970 Roman
(Continued)

FOREIGN PATENT DOCUMENTS

CA 2448220 A1 1/2003
CN 1976632 A 6/2007
(Continued)

OTHER PUBLICATIONS

Garmin Corporation, "GPS II: Owner's Manual & Reference (Garmin)," 1996.
(Continued)

*Primary Examiner* — Lee S Cohen
*Assistant Examiner* — Erin M Cardinal
(74) *Attorney, Agent, or Firm* — Sterne, Kessler, Goldstein & Fox P.L.L.C.

(57) ABSTRACT

The present invention provides a sensor garment including a harness. In one exemplary embodiment, the sensor garment includes a textile portion, a device-retention element coupled to the textile portion, and a stretchable harness coupled to the textile portion. The harness includes a conductive element disposed between layers of film. The conductive element includes a first termination point at the device retention element, configured to connect to a monitor device. The conductive element includes a second termination point configured to connect to a sensor or transceiver.

24 Claims, 28 Drawing Sheets

(51) Int. Cl.
*A61B 5/0205* (2006.01)
*A41D 1/00* (2018.01)
*A41D 13/00* (2006.01)
*A63B 24/00* (2006.01)
*A61B 5/0408* (2006.01)
*A61B 5/01* (2006.01)
*A61B 5/0402* (2006.01)
*A61B 5/053* (2006.01)
*A61B 5/08* (2006.01)
*A61B 5/11* (2006.01)

(52) U.S. Cl.
CPC ........ *A61B 5/6831* (2013.01); *A63B 24/0062* (2013.01); *A61B 5/01* (2013.01); *A61B 5/0402* (2013.01); *A61B 5/0537* (2013.01); *A61B 5/0816* (2013.01); *A61B 5/11* (2013.01); *A61B 5/4875* (2013.01); *A61B 2562/221* (2013.01); *A63B 2024/0025* (2013.01); *A63B 2024/0071* (2013.01); *A63B 2220/836* (2013.01); *A63B 2230/00* (2013.01)

(56) References Cited

U.S. PATENT DOCUMENTS

| | | |
|---|---|---|
| 3,743,559 A | 7/1973 | Duby et al. |
| 3,874,368 A | 4/1975 | Asrican |
| 3,926,177 A | 12/1975 | Hardway, Jr. et al. |
| 4,016,868 A | 4/1977 | Allison |
| 4,033,332 A | 7/1977 | Hardway, Jr. et al. |
| 4,102,331 A | 7/1978 | Grayzel et al. |
| 4,202,350 A | 5/1980 | Walton |
| 4,289,142 A | 9/1981 | Kearns |
| 4,308,872 A | 1/1982 | Watson et al. |
| 4,312,358 A | 1/1982 | Barney |
| 4,373,534 A | 2/1983 | Watson |
| 4,387,722 A | 6/1983 | Kearns |
| 4,494,553 A | 1/1985 | Sciarra et al. |
| 4,572,197 A | 2/1986 | Moore et al. |
| 4,580,572 A | 4/1986 | Granek et al. |
| 4,753,088 A * | 6/1988 | Harrison ................ D04B 21/12 2/125 |
| 4,777,962 A | 10/1988 | Watson et al. |
| 4,815,473 A | 3/1989 | Watson et al. |
| 4,817,625 A | 4/1989 | Miles |
| 4,889,131 A | 12/1989 | Salem et al. |
| 4,909,260 A | 3/1990 | Salem et al. |
| 4,962,469 A | 10/1990 | Ono et al. |
| 5,007,427 A | 4/1991 | Suzuki et al. |
| 5,074,129 A | 12/1991 | Matthew |
| 5,076,801 A | 12/1991 | Schroll |
| 5,099,855 A | 3/1992 | Yount |
| 5,111,818 A | 5/1992 | Suzuki et al. |
| 5,143,089 A | 9/1992 | Alt |
| 5,148,002 A | 9/1992 | Kuo et al. |
| 5,153,584 A | 10/1992 | Engira |
| 5,159,935 A | 11/1992 | Sackner et al. |
| 5,204,670 A | 4/1993 | Stinton |
| 5,210,540 A | 5/1993 | Masumoto |
| 5,241,300 A | 8/1993 | Buschmann |
| 5,295,490 A | 3/1994 | Dodakian |
| 5,329,932 A | 7/1994 | Yount |
| 5,348,008 A | 9/1994 | Bornn et al. |
| 5,353,793 A | 10/1994 | Bornn |
| 5,388,584 A | 2/1995 | King |
| 5,400,254 A | 3/1995 | Fujita |
| 5,416,961 A | 5/1995 | Vinay |
| 5,428,546 A | 6/1995 | Shah et al. |
| 5,454,376 A | 10/1995 | Stephens et al. |
| 5,583,776 A | 12/1996 | Levi et al. |
| 5,611,085 A | 3/1997 | Rasmussen |
| 5,635,909 A * | 6/1997 | Cole ................ A62B 17/003 2/93 |
| 5,724,025 A | 3/1998 | Tavori |
| 5,758,313 A | 5/1998 | Shah et al. |
| 5,769,755 A | 6/1998 | Henry et al. |
| 5,782,778 A | 7/1998 | De Briere et al. |
| 5,820,567 A | 10/1998 | Mackie |
| 5,862,511 A | 1/1999 | Croyle et al. |
| 5,937,854 A | 8/1999 | Stenzler |
| 5,991,922 A | 11/1999 | Banks |
| 6,002,982 A | 12/1999 | Fry |
| 6,047,203 A | 4/2000 | Sackner et al. |
| 6,066,093 A | 5/2000 | Kelly et al. |
| 6,070,269 A * | 6/2000 | Tardif ................ G06F 3/011 2/69 |
| 6,145,551 A | 11/2000 | Jayaraman et al. |
| 6,148,262 A | 11/2000 | Fry |
| 6,179,786 B1 | 1/2001 | Young |
| 6,198,394 B1 | 3/2001 | Jacobsen et al. |
| 6,246,362 B1 | 6/2001 | Tsubata et al. |
| 6,254,551 B1 | 7/2001 | Varis |
| 6,266,623 B1 | 7/2001 | Vock et al. |
| 6,287,264 B1 | 9/2001 | Hoffman |
| 6,306,088 B1 | 10/2001 | Krausman et al. |
| 6,341,504 B1 | 1/2002 | Istook |
| 6,381,482 B1 | 4/2002 | Jayaraman et al. |
| 6,419,636 B1 | 7/2002 | Young et al. |
| 6,424,295 B1 | 7/2002 | Lange |
| 6,443,890 B1 | 9/2002 | Schulze et al. |
| 6,461,307 B1 | 10/2002 | Kristbjarnarson et al. |
| 6,463,385 B1 | 10/2002 | Fry |
| 6,478,736 B1 | 11/2002 | Mault |
| 6,513,532 B2 | 2/2003 | Mault et al. |
| 6,529,827 B1 | 3/2003 | Beason et al. |
| 6,551,252 B2 | 4/2003 | Sackner et al. |
| 6,579,231 B1 | 6/2003 | Phipps |
| 6,616,613 B1 | 9/2003 | Goodman |
| 6,687,523 B1 * | 2/2004 | Jayaramen ........ A41D 13/1281 600/388 |
| 6,790,178 B1 | 9/2004 | Mault et al. |
| 6,798,378 B1 | 9/2004 | Walters |
| 6,941,775 B2 | 9/2005 | Sharma |
| 6,970,731 B1 | 11/2005 | Jayaramen et al. |
| 7,069,089 B2 * | 6/2006 | Minogue ................ A61N 1/321 600/390 |
| 7,254,516 B2 | 8/2007 | Case, Jr. et al. |
| 7,559,902 B2 | 7/2009 | Ting et al. |
| 7,604,603 B2 | 10/2009 | Sackner et al. |
| 7,670,295 B2 | 3/2010 | Sackner et al. |
| 7,680,523 B2 | 3/2010 | Rytky |
| 7,715,982 B2 | 5/2010 | Grenfell et al. |
| 7,850,574 B2 | 12/2010 | Narayanaswami |
| 8,034,001 B2 | 10/2011 | Gal |
| 8,818,478 B2 * | 8/2014 | Scheffler ................ A41D 1/002 600/388 |
| 2002/0032386 A1 | 3/2002 | Sackner et al. |
| 2004/0010420 A1 | 1/2004 | Rooks |
| 2004/0176674 A1 | 9/2004 | Nazeri |
| 2005/0010096 A1 | 1/2005 | Blackadar |
| 2005/0054941 A1 * | 3/2005 | Ting ........ A61B 5/0408 600/529 |
| 2005/0067007 A1 | 3/2005 | Toft |
| 2005/0275416 A1 * | 12/2005 | Hervieux ........ A41D 13/1281 324/663 |
| 2006/0124193 A1 | 6/2006 | Orr et al. |
| 2006/0135863 A1 | 6/2006 | Birnbaum et al. |
| 2007/0038057 A1 | 2/2007 | Nam et al. |
| 2007/0089800 A1 | 4/2007 | Sharma |
| 2007/0299325 A1 | 12/2007 | Farrell et al. |
| 2008/0015454 A1 | 1/2008 | Gal |
| 2008/0287770 A1 | 11/2008 | Kurzweil et al. |
| 2009/0082835 A1 | 3/2009 | Jaax et al. |
| 2009/0088652 A1 | 4/2009 | Tremblay |
| 2009/0227856 A1 | 9/2009 | Russell et al. |
| 2009/0306485 A1 | 12/2009 | Bell |
| 2010/0185076 A1 * | 7/2010 | Jeong ........ A61B 5/0408 600/388 |
| 2010/0198043 A1 | 8/2010 | Holzer et al. |
| 2010/0234715 A1 | 9/2010 | Shin et al. |
| 2010/0274100 A1 | 10/2010 | Behar et al. |
| 2011/0054270 A1 | 3/2011 | Derchak |
| 2011/0054271 A1 | 3/2011 | Derchak et al. |

(56) References Cited

U.S. PATENT DOCUMENTS

| | | | |
|---|---|---|---|
| 2011/0054272 A1 | 3/2011 | Derchak | |
| 2011/0054289 A1 | 3/2011 | Derchak et al. | |
| 2011/0054290 A1 | 3/2011 | Derchak | |
| 2011/0087115 A1 | 4/2011 | Sackner et al. | |
| 2011/0105861 A1 | 5/2011 | Derchak et al. | |
| 2011/0130643 A1 | 6/2011 | Derchak et al. | |
| 2012/0071793 A1* | 3/2012 | Gal | A61B 5/1135 600/595 |
| 2012/0144561 A1* | 6/2012 | Begriche | D04B 1/22 2/243.1 |
| 2012/0253484 A1 | 10/2012 | Burich | |
| 2012/0254934 A1 | 10/2012 | McBrearty et al. | |
| 2013/0018251 A1* | 1/2013 | Caprio | A61B 5/6832 600/393 |
| 2013/0041590 A1 | 2/2013 | Burich et al. | |
| 2014/0180624 A1* | 6/2014 | Nikonov | G01K 7/16 702/130 |

FOREIGN PATENT DOCUMENTS

| | | |
|---|---|---|
| DE | 102 51 900 A1 | 5/2004 |
| EP | 1 134 555 A1 | 9/2001 |
| EP | 2 042 093 A1 | 4/2009 |
| GB | 2 170 680 | 8/1986 |
| JP | 2008-541311 A | 11/2008 |
| JP | 2009-105027 A | 5/2009 |
| JP | 2011-104351 A | 6/2011 |
| WO | WO 86/04497 A1 | 8/1986 |
| WO | WO 2002/067449 A2 | 8/2002 |
| WO | WO 02071935 | 9/2002 |
| WO | WO 2006/00345 A2 | 1/2006 |
| WO | WO2006/125186 A2 | 11/2006 |
| WO | WO 2009 013704 | 1/2009 |
| WO | WO 2009/148595 A2 | 12/2009 |
| WO | WO2012/073230 A1 | 6/2012 |

OTHER PUBLICATIONS

U.S. Appl. No. 11/357,772, inventors Sackner et al., filed Feb. 17, 2006.

U.S. Appl. No. 11/373,822, inventors Sackner et al., filed Mar. 9, 2006.

International Search Report and Written Opinion for International Patent Application No. PCT/CA2012/050244, dated Jun. 27, 2012, 10 pages.

Fraunhofer Microelectronics, "The Knitting Machine Meets the Silicon Chip," <www.mikroelektronik.fraunhofer.de/en/press-media>, dated Sep. 27, 2010, 4 pages.

* cited by examiner

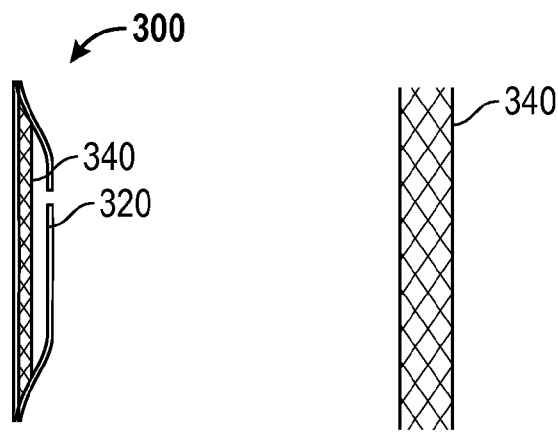
FIG. 13     FIG. 14
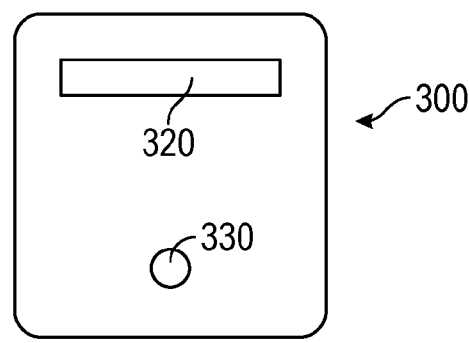
FIG. 15
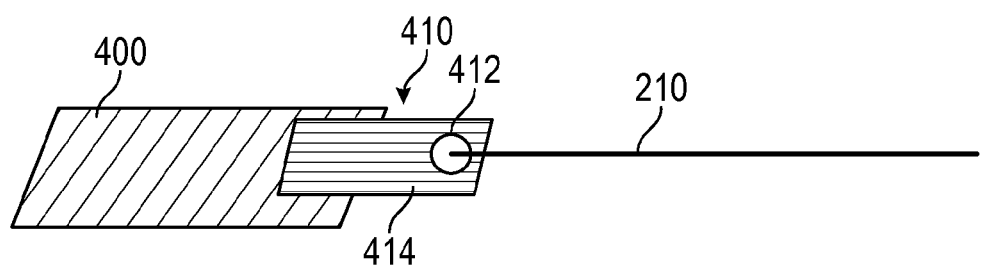
FIG. 16

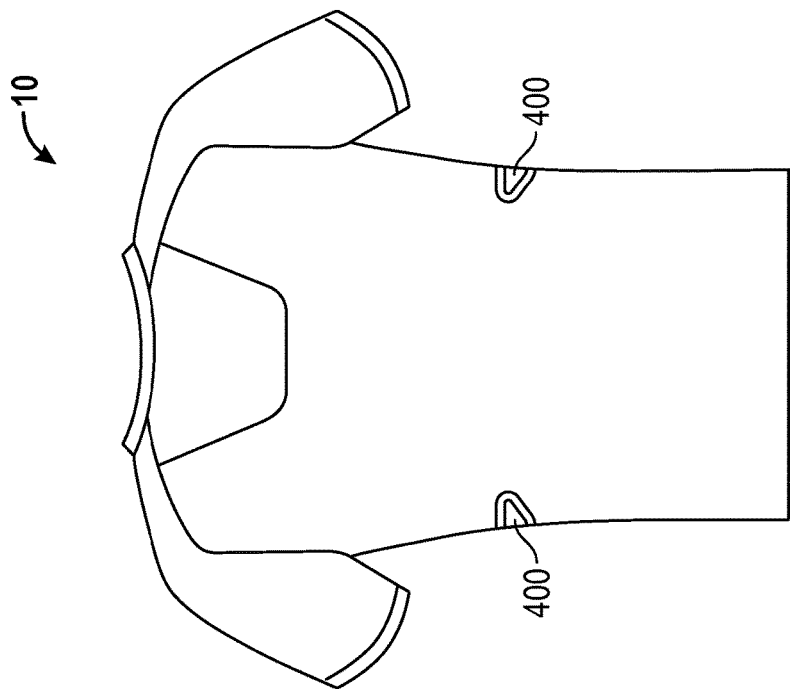
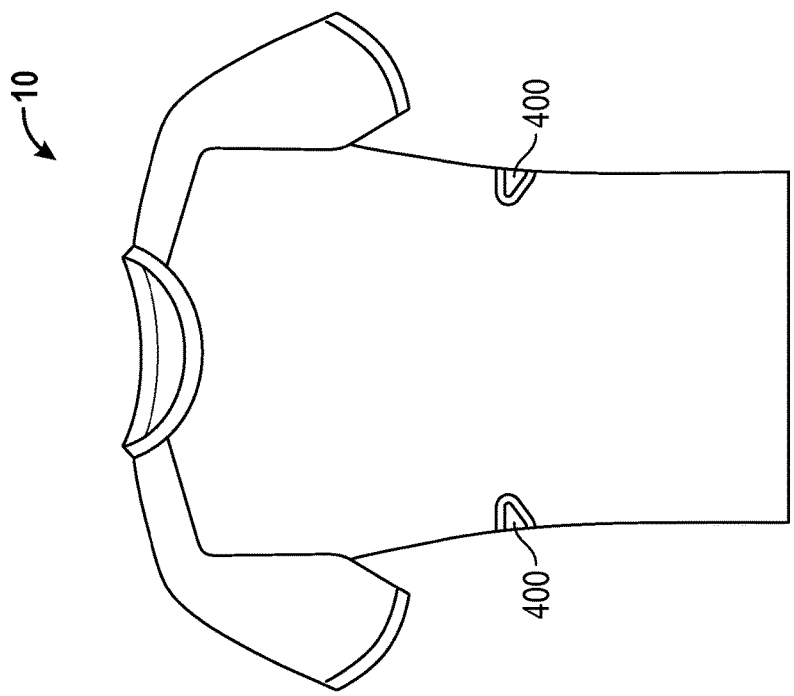

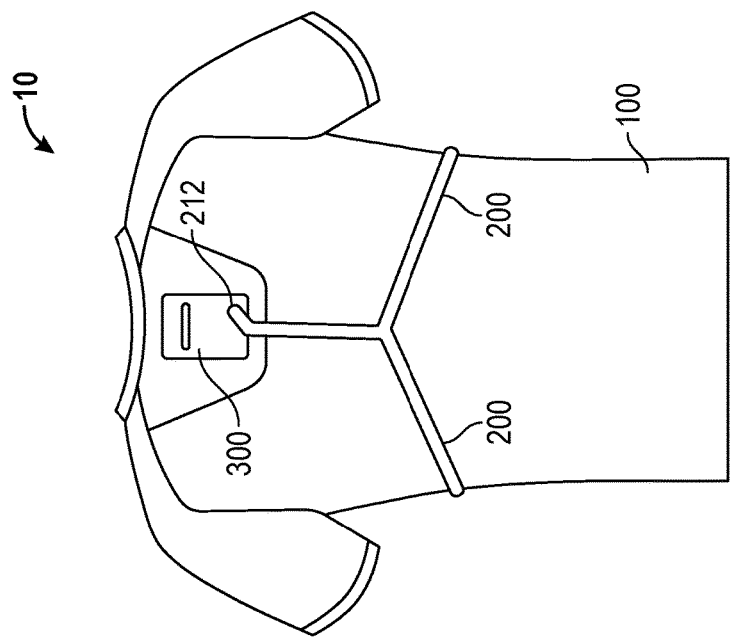
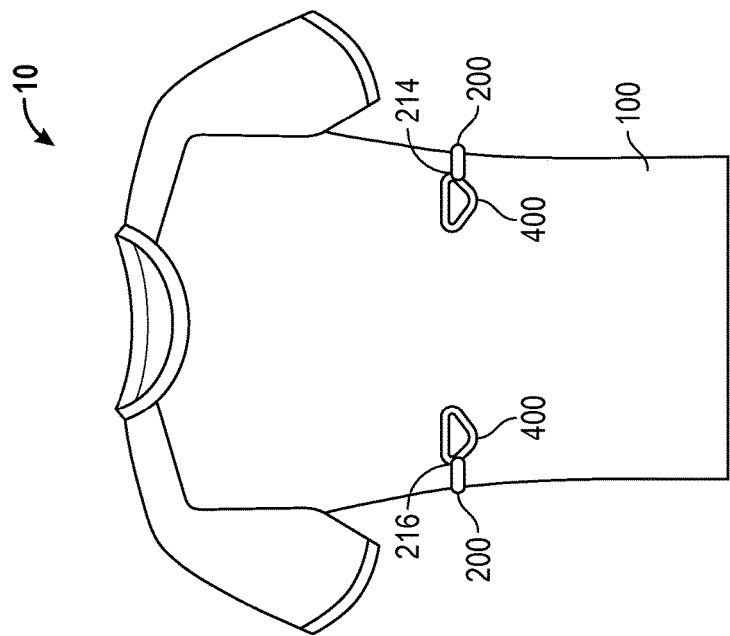

SENSOR GARMENT

CROSS-REFERENCE TO RELATED APPLICATION

This application is a continuation of U.S. patent application Ser. No. 13/077,520, now U.S. Pat. No. 8,818,478, filed Mar. 31, 2011, titled "Sensor Garment," which is incorporated herein in its entirety by reference thereto.

BACKGROUND OF THE INVENTION

Field of the Invention

The present invention generally relates to a harness and a garment, and in particular to a garment for use with sensors.

Background Art

Exercise is important to maintaining a healthy lifestyle and individual well-being. A common way for individuals to exercise is to participate in athletic activities, such as, for example, sports and training programs. A session of athletic activity may include, for example, a training session or a competitive session such as, for example, a soccer match or basketball game. When participating in athletic activities in a competitive or collaborative environment, one's performance may be dependent on the performance of other individuals. For example, in a team sport context, the performance of various athletic movements and endeavors may be influenced by the athletic movements and endeavors of teammates or adversaries. Often, a trainer (e.g., a coach) is monitoring such athletic activity.

To effectively monitor an individual or group of individuals participating in the athletic activity, the trainer, or other individual, typically gathers information about the participants in the athletic activity by viewing the athletic activity from, for example, the sidelines of a sports field. Thus, the information used to make decisions that influence the athletic activity is typically limited by what is observed by the trainer from the sidelines. A trainer may have assistants to help with this observation, or multiple trainers may work together, however there remains difficulty in monitoring a plurality of individuals so as to effectively track and manage performance of individuals during an athletic activity.

BRIEF SUMMARY OF THE INVENTION

The present invention provides a harness and a sensor garment including a harness. In one exemplary embodiment, the sensor garment includes a textile portion, a device-retention element coupled to the textile portion, and a stretchable harness coupled to the textile portion, the stretchable harness comprising an electrically conductive element having a first termination point at the device retention element and a second termination point.

In another exemplary embodiment, the harness includes a stretchable first layer, a stretchable second layer coupled to the first layer, and a stretchable electrically conductive element disposed between the first layer and the second layer having a first termination point, configured to connect to a monitor device, and a second termination point configured to connect to a first sensor for sensing a physiological parameter of a wearer of the garment.

In another exemplary embodiment, the sensor garment includes a textile portion, a device retention element coupled to a first area of the textile portion configured to be proximate to the back of a wearer of the garment, a first sensor coupled to a second area of the textile portion configured to be proximate to a right side of the torso of the wearer, a second sensor coupled to a third area of the textile portion configured to be proximate to a left side of the torso of the wearer, and a harness bonded to the textile portion. The harness includes a first harness portion extending between the first area and the second area, and configured to couple to the first sensor, and a second harness portion extending between the first harness portion and the third area, and configured to couple to the second sensor.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention. In the drawings, like reference characters indicate identical or functionally similar elements.

FIG. 13 is a sectional side view of a device retention element according to an exemplary embodiment of the present invention.

FIG. 14 is an enlarged side view of a support element according to an exemplary embodiment of the present invention.

FIG. 15 is a perspective view of a device retention element according to an exemplary embodiment of the present invention.

FIG. 16 is a perspective view of a sensor according to an exemplary embodiment of the present invention.

FIG. 32 is a perspective front view of a garment according to an exemplary embodiment of the present invention.

FIG. 33 is a perspective rear view of the garment of FIG. 32 according to an exemplary embodiment of the present invention.

FIG. 45 is a perspective front view of a garment according to an exemplary embodiment of the present invention.

FIG. 46 is a perspective rear view of the garment of FIG. 45 according to an exemplary embodiment of the present invention.

DETAILED DESCRIPTION OF THE INVENTION

Figure 1:
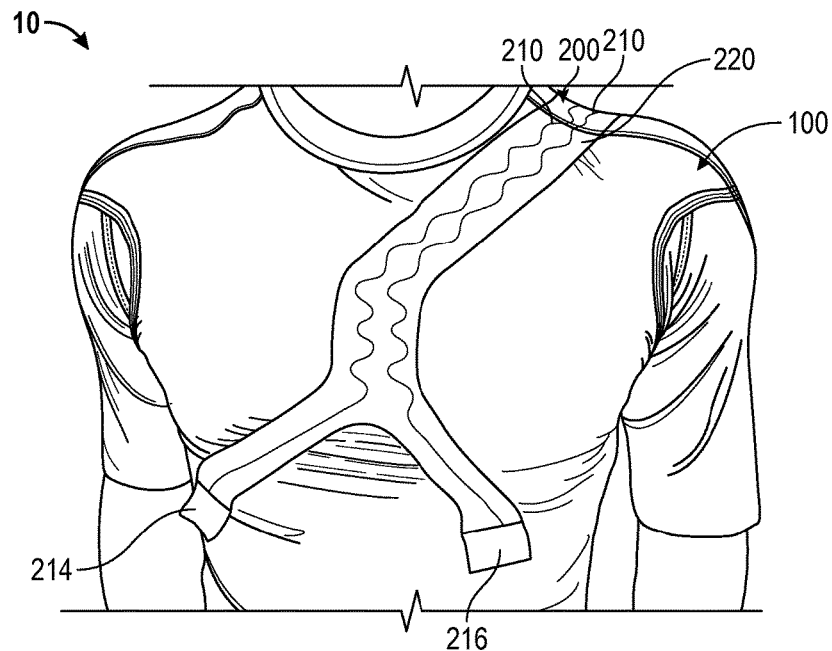
FIG. 1 is a perspective front view of a garment, shown inside-out, according to an exemplary embodiment of the present invention.

The present invention will now be described in detail with reference to embodiments thereof as illustrated in the accompanying drawings. References to "one embodiment", "an embodiment", "an exemplary embodiment", "some exemplary embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The term "invention" or "present invention" as used herein is a non-limiting term and is not intended to refer to any single embodiment of the particular invention but encompasses all possible embodiments as described in the application.

In an exemplary embodiment of the present invention, a sensor garment 10 is provided. Sensor garment 10 may include a textile portion 100, a harness 200, and a device retention element 300. In some exemplary embodiments, sensor garment 10 includes at least one sensor 400. FIGS. 1-8, 11, 12, 24, 25, 29-33 and 35-46 depict sensor garments 10 according to exemplary embodiments of the present invention.

Sensor garment 10 may be adapted to be worn by a wearer. Sensors 400, which may be positioned at ends of harness 200, may sense physiological or performance characteristics of the wearer. Physiological characteristics may be indicative of conditions of the wearer's body (e.g., heart rate, body temperature, respiration rate, hydration status). Performance characteristics may be indicative of performance of the wearer's body with respect to a parameter of interest (e.g., speed, orientation, direction, acceleration, position, fatigue, impact, efficiency), and may take into account physiological characteristics. Further, sensors 400 may transmit data indicative of these characteristics, via harness 200, to a monitor device 500 positioned at an end of harness 200.

Monitor device 500 may be any device capable of receiving data. Monitor device 500 may perform a variety of operations. For example, monitor device 500 may store the received data, may process it, or may transmit it to a reception device. In some exemplary embodiments, monitor device 500 and the reception device are such as the individual monitor and base station, respectively, disclosed in commonly owned U.S. patent application Ser. No. 13/077, 494, filed Mar. 31, 2011, entitled Group Performance Monitoring System and Method, the disclosure of which is hereby incorporated in its entirety by reference thereto. In some exemplary embodiments, monitor device 500 is small enough to be easily carried by the wearer, via device retention element 300 of sensor garment 10, without causing substantial discomfort or restriction of motion of the wearer.

Figures 26, 27:
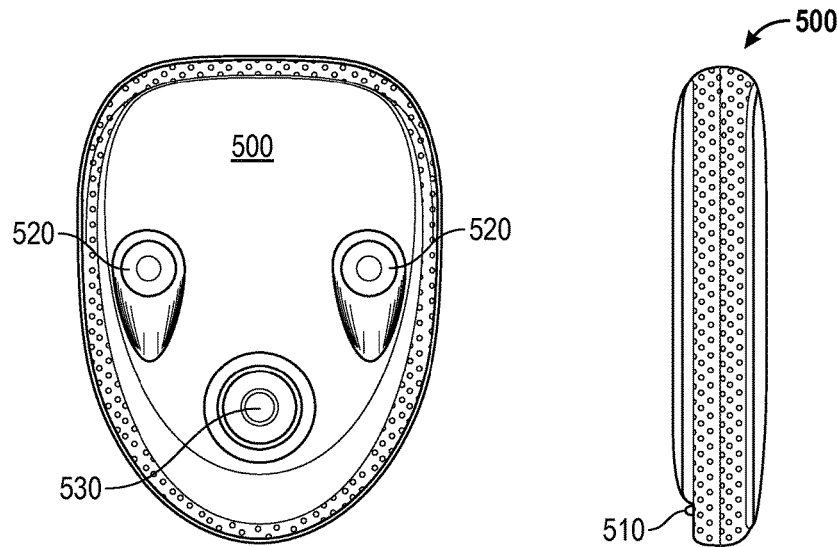
FIG. 26 is a perspective front view of a monitor device according to an exemplary embodiment of the present invention.
FIG. 27 is a perspective side view of the monitor device of FIG. 26 according to an exemplary embodiment of the present invention.
Figure 28:
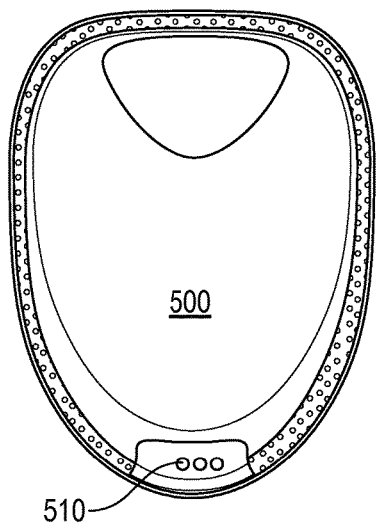
FIG. 28 is a perspective rear view of the monitor device of FIG. 26 according to an exemplary embodiment of the present invention.

In some exemplary embodiments, monitor device 500 may be a pod-like device, as shown in the exemplary embodiment of FIGS. 26-28, and may include a universal serial bus (USB) port 510, at least one data port 520, and a display and/or control 530. Monitor device may further include at least one of a battery, a position module, a heart rate monitor module, a controller, a user interface, a transceiver, an antenna, an acceleration sensor module, a memory, a gyroscope module, a magnetometer module, a respiration module, a light sensor module, and a temperature sensor module. Monitor device 500 may itself include sensors to correspond to these modules, or may be connected to distinct sensors 400 via harness 200. The sensors and corresponding modules discussed herein are exemplary only; other sensors and modules can be used in conjunction with embodiments of the present invention. The battery may provide power to monitor device 500.

Data port 520 may facilitate information transfer to and from monitor device 500 and may connect to a termination point of conductive elements 210 of harness 200, described below. Data port 520 may include any suitable connection to connect to conductive element 210. In some exemplary embodiments, data port 520 includes one or more terminals configured to individually connect to conductive elements 210. In some exemplary embodiments, data port 520 may be a universal serial bus (USB) port. In some exemplary embodiments, the transceiver of monitor device 500 may include data transmitting and receiving capability and may include a single component or separate components. In the exemplary embodiment of FIGS. 26-28, monitor device 500 is depicted as a pod-like device. Monitor device 500 may be, however, any other suitable device, such as, for example, a smartphone, a mobile phone, an e-reader, a PDA (personal digital assistant), or other similar device capable receiving and transmitting data.

In use, the wearer, who may be an athlete engaged in an athletic activity, may wear sensor garment 10 in order to monitor (or facilitate another's monitoring of) his performance. Physiological and performance characteristic data indicative of such performance may be received at sensors 400, transmitted (via harness 200) to monitor device 500 retained by device retention element 300, and transmitted by monitor device 500 to a remote reception device.

Figure 9:
FIG. 9 is a perspective front view of a jersey according to an exemplary embodiment of the present invention.
Figure 10:
FIG. 10 is a perspective rear view of the jersey of FIG. 9 according to an exemplary embodiment of the present invention.
Figure 11:
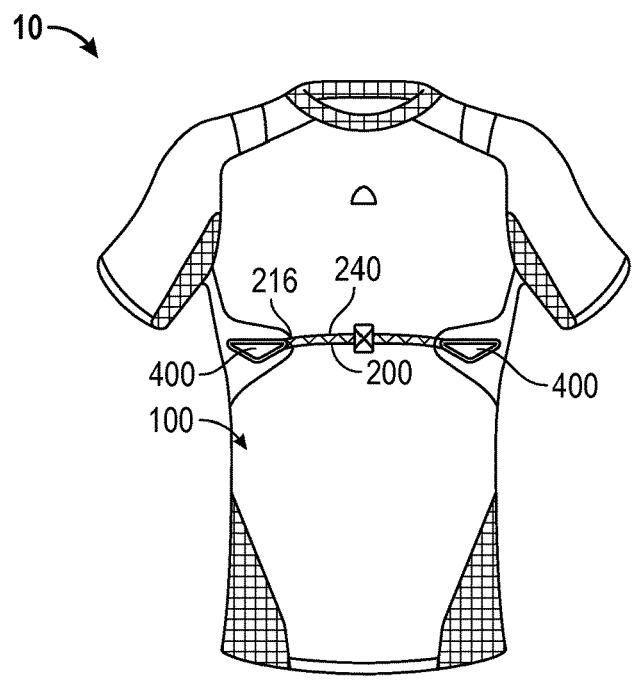
FIG. 11 is a perspective front view of a garment according to an exemplary embodiment of the present invention.
Figure 12:
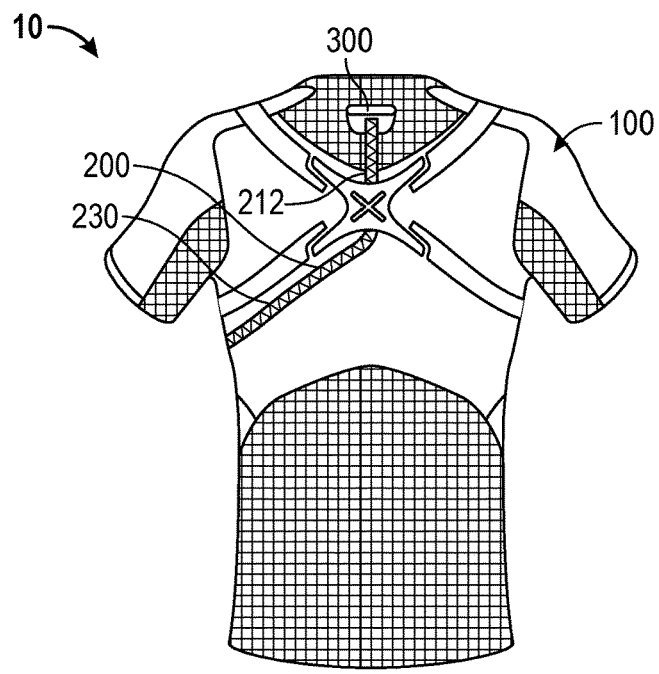
FIG. 12 is a perspective rear view of the garment of FIG. 11 according to an exemplary embodiment of the present invention.

In one embodiment, sensor garment 10 may comprise a shirt (as depicted in the figures). In some exemplary embodiments, sensor garment 10 may comprise a garment, such as, for example, a vest, a compression shirt, suspenders, a band, a strap, a shoulder harness, a shirt with a compression base layer, a jersey, a tank top, a bra, a sleeve, an arm band, a head band, a hat, a tube top, shorts, briefs, pants, socks, jackets, outerwear, swimsuits, wetsuits, and other suitable garments or apparel and portions thereof. In one embodiment, one or more features of sensor garment 10 may be incorporated into footwear. In some exemplary embodiments, sensor garment 10 is designed to be worn without another garment worn over sensor garment 10. In some exemplary embodiments, sensor garment 10 is designed to be worn with another garment worn over garment 10, such as, for example, jersey 20, as shown, for example, in FIGS. 9 and 10.

Textile portion 100 may form the shape and fit of sensor garment 10, and may be designed to fit any portion of a wearer's body. In some exemplary embodiments the wearer is a human; however, embodiments of the present invention can apply to nonhuman animate beings as well. In some exemplary embodiments, textile portion 100 is designed to fit snugly to the wearer's body (i.e., designed so that an interior surface of textile portion 100 is in contact with the wearer's body throughout expected motion of the body). In order to support optimum or desired fit, textile portion 100 may include elastic portions, as well as inelastic portions.

Figure 2:
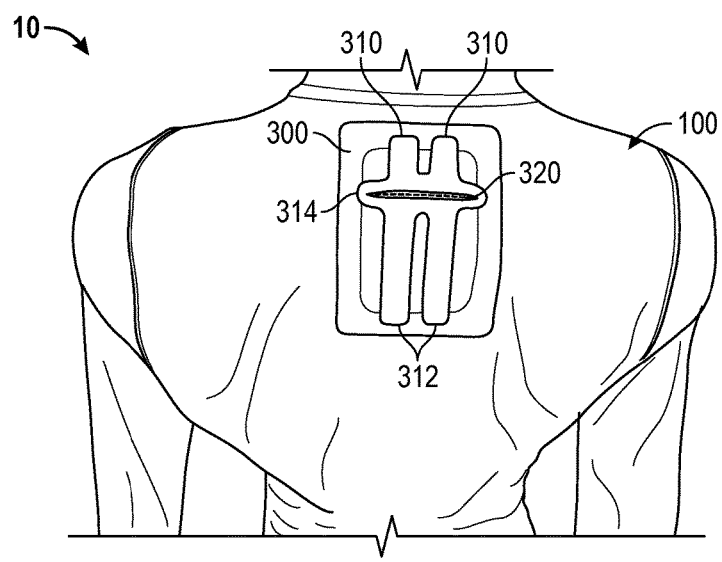
FIG. 2 is a perspective rear view of a garment according to an exemplary embodiment of the present invention.

With reference to FIG. 2, textile portion 100 may include a device retention element 300 configured to retain a device, such as monitor device 500, that can receive data (via harness 200) and transmit data to a reception device. In some exemplary embodiments, device retention element 300 is sized and shaped to correspond to the size and shape of monitor device 500, to be capable of nesting monitor device 500 therein and holding monitor device 500 in place so as to minimize the effect of movement of a wearer of sensor garment 10 on monitor device 500. Additional elements may be used to help minimize this effect, such as, for example, bands 312 and spacer element 340, discussed further herein. As shown in FIG. 2, device retention element 300 may be coupled to textile layer 100. FIG. 2 depicts an exemplary embodiment of sensor garment 10, including device retention element 300 coupled to textile layer 100. Device retention element 300 may be coupled to textile layer 100 by, for example, being integral therewith, being adhered, stitched, welded, tied, clipped, snapped, or mounted thereto, or any combination of these and other techniques. In some exemplary embodiments, device retention element is formed integrally with textile layer 100 (e.g., textile layer 100 may be stitched or knitted to form a pocket therein).

In the exemplary embodiment of FIG. 2, device retention element 300 is a pocket formed by a fabric layer having opening 320, positioned on an exterior of textile layer 100. In some exemplary embodiments, device retention element 300 is a pocket formed by a fabric layer having opening 320, positioned on an interior of textile layer 100. In some exemplary embodiments, device retention element 300 is a pocket formed by a fabric layer not having opening 320, positioned on an interior of textile layer 100. In such an embodiment, textile layer 100 may include opening 320 providing access to the pocket from the exterior of textile layer 100. In some exemplary embodiments, device retention element 300 is a complete pocket, attached to the exterior or interior of, or integrated within, textile layer 100. In some exemplary embodiments, rather than being formed of fabric, device retention element 300 is formed at least partially of other materials, for example, plastic, rubber, thermoplastic polyurethane, or neoprene.

In the exemplary embodiment of FIG. 2, device retention element 300 is positioned to correspond to the upper back of a wearer of sensor garment 10. Positioning device retention element 300 to correspond to a high position on the wearer, such as the upper back, may help minimize interference and maximize range and signal strength of monitor device 500 within device retention element 300 when monitor device 500 sends or receives data. Additionally, positioning device retention element 300 to correspond to the upper back minimizes interference with athlete movements by device retention element 300 (and monitor device 500 retained thereby). In some exemplary embodiments, device retention element 300 is positioned to correspond to other than the upper back of a wearer. Device retention element 300 can be positioned anywhere on textile layer 100. For example, device retention element 300 may be positioned to correspond to the lower back, chest, side, shoulder, arm, leg, posterior, foot, neck, or head of a wearer.

In some exemplary embodiments, device retention element 300 is other than a pocket. For example, device retention element may include, for example, a mount, a snap, a tie, a button, a lattice, or a clip. Device retention element 300 may retain monitor device 500 in a variety of ways, for example, monitor device 500 may be disposed within, coupled to, hanging from, or mounted in device retention element 300. Device retention element 300 may be positioned on the exterior of textile layer 100, as shown in FIG. 2. In some exemplary embodiments, device retention element 300 is positioned other than on the exterior of textile layer 100. For example, device retention element 300 may be positioned on an interior of textile layer 100, or integrated within textile layer 100. In some exemplary embodiments, textile layer 100 includes multiple layers. In such an embodiment, device retention element 300 may be positioned between layers of textile layer 100, on a top surface of an outer layer or an inner layer, or on a bottom surface of an outer layer or an inner layer. FIGS. 13, 15, and 20-23 depict further exemplary embodiments of device retention element 300 as discussed below.

As shown in FIG. 2, for example, device retention element 300 may include an opening 320 for insertion and removal of monitoring device 500. In some embodiments opening 320 is sealable, for example, by a zipper, hook-and-loop fastener, ties, snaps, buttons, or other suitable closing elements. Device retention element may include holes 330, which may provide windows to view portions of monitor device 500 while it is retained by device retention element 300. For example, if monitor device 500 includes a display and/or control 530 (e.g., an LCD (liquid crystal display) display, LED (light emitting diode) display, individual LEDs, e-ink, a switch, or a button), holes 330 may provide access to display and/or control 530.

Device retention element 300 may include a support element 310, as in the exemplary embodiment of FIG. 2, which may provide support to device retention element 300 by, for example, increasing resistance to movement, increasing stability, and increasing wear-resistance. Support element 310 may also help maintain the position of monitor device 500 within or in relation to device retention element 300.

In the exemplary embodiment of FIG. 2, support element 310 is a TPU (thermoplastic polyurethane) layer patterned on the exterior surface of device retention element 300. Such a support element 310 may be laminated on or within device retention element 300. In some exemplary embodiments, support element 310 may be printed onto device retention element 300, or may be an elastic (e.g., rubber) band integrated into device retention 300. In FIG. 2, support element 310 particularly supports the area around opening 320. This may help to minimize wear around opening 320 that may result from repeated insertion and removal of monitor device 500. Support element 310 may include, as in the exemplary embodiment of FIG. 2, vertical bands 312 that particularly support vertical segments of device retention element 300. This may help to minimize movement of monitor device 500 in the vertical direction, which may be desirable during athletic activity of a wearer, when substantial vertical forces, due to, for example, running, are incident on monitor device 500. Support element 310 may further include an opening support element 314 disposed about opening 320, which may provide support and/or facilitate access to the area.

In the exemplary embodiment of FIG. 2, support element 310 only partially covers an exterior surface of device retention element 300. In some exemplary embodiments, support element 310 completely covers the exterior and/or interior surface of device retention element 300.

Figure 20:
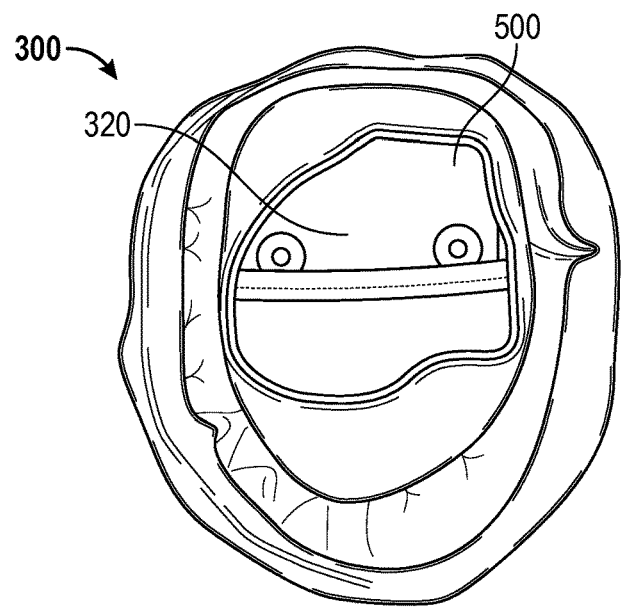
FIG. 20 is a perspective view of a device retention element according to an exemplary embodiment of the present invention.
Figure 21:
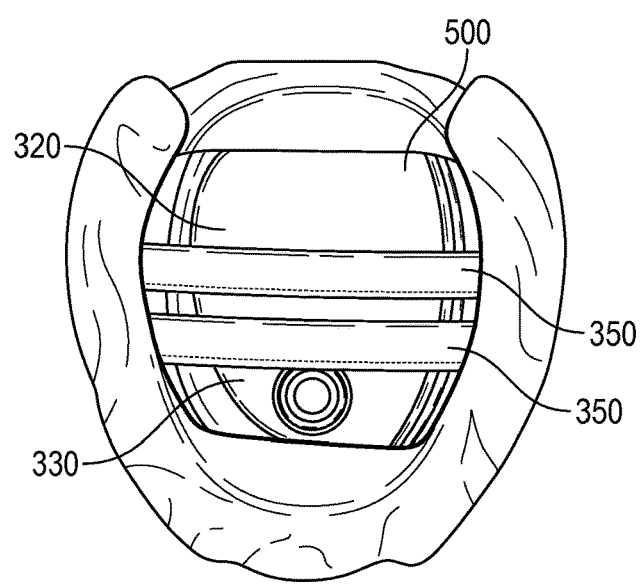
FIG. 21 is a perspective view of a device retention element according to an exemplary embodiment of the present invention.
Figure 22:
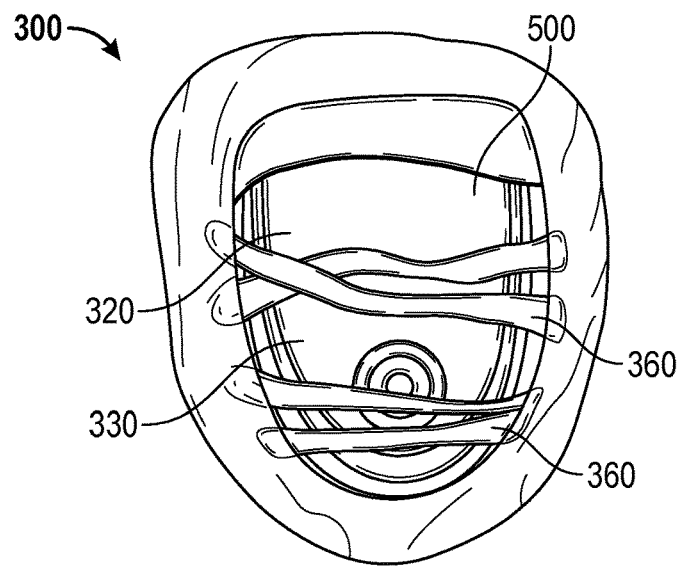
FIG. 22 is a perspective view of a device retention element according to an exemplary embodiment of the present invention.
Figure 23:
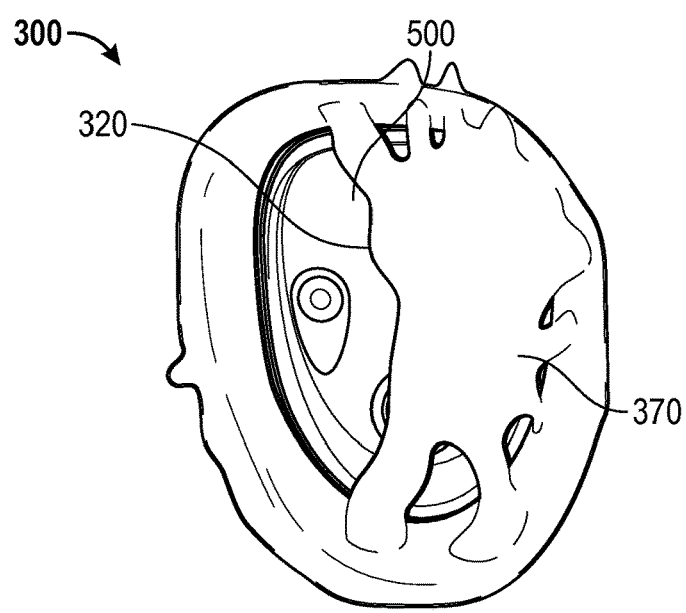
FIG. 23 is a perspective view of a device retention element according to an exemplary embodiment of the present invention.

Device retention element 300 can be provided according to a variety of embodiments. In one exemplary embodiment, as shown in FIG. 13, device retention element 300 may comprise a pocket including spacer element 340, which will be discussed in more detail below. In one exemplary embodiment, as shown in FIG. 15, device retention element 300 may comprise a pocket including opening 320 as an elongated opening for receiving monitor device 500 therethrough, and one or more holes 330 configured to correspond to features of monitor device 500, for example, display and/or control 530, shown in FIG. 26, for example. In one exemplary embodiment, as shown in FIG. 20, device retention element 300 may comprise a pocket including opening 320 sized and arranged to display features of monitor device. In the exemplary embodiment of FIG. 20 device retention element 300 includes no holes 330. In one exemplary embodiment, as shown in FIG. 21, device retention element 300 may comprise elastic bands 350 configured to hold monitor device 500 in place. In the exemplary embodiment of FIG. 21, spaces between elastic bands 350 may act as holes 330. In one exemplary embodiment, as shown in FIG. 22, device retention element 300 may comprise ties or laces 360. In the exemplary embodiment of FIG. 22, monitor device 500 can be inserted via opening 320 between laces 360, and laces can be tightened or loosened in order to achieve a desired fit of monitor device 500 within device retention element 300. In one exemplary embodiment, as shown in FIG. 23, device retention element 300 may comprise a web covering 370, which provides access through opening 320 in the side of device retention element 300.

Sensor garment 10 may be worn by an athlete during a session of athletic activity. During such activity, monitor device 500 retained by device retention element 300 may be subject to a wide variety of incident forces, due to the motion of the athlete. In some exemplary embodiments, device retention element 300 includes a spacer element 340, which can provide padding between monitor device 500 and the wearer, can help dampen and control movement of monitor device 500, can reduce shock and/or shear forces on monitor device 500, and can minimize injury to the wearer in the event of impact at or proximate to monitor device 500. As shown in FIGS. 13 and 14, in some exemplary embodiments, where device retention element 300 is a pocket, spacer element 340 may be positioned inside or on the pocket, for example, configured to be positioned between an interior area of the pocket a wearer of sensor garment 10. Spacer element 340 may be coupled to textile layer 100 on at least one surface. Spacer element 340 may be a three-dimensional mesh or foam that dampens shear forces, thereby minimizing incident forces on monitor device 500, and minimizing discomfort to the wearer of garment 10.

In some exemplary embodiments, monitor device 500 is configured to receive data from sensors 400, which may be included in monitor device 500, or may be separate and distinct from monitor device 500 (e.g., coupled to textile layer 100 or the wearer of sensor garment 10). In some exemplary embodiments, such as those depicted in FIGS. 3 and 4, for example, sensor garment 10 may include a device retention element 300 located at an upper back of a wearer of sensor garment 10, configured to retain monitor device 500, and may include a sensor 400 configured to be positioned proximate a side of a torso of the wearer. Sensor garment 10 may include any suitable number or type of sensors 400, as desired or required. For example, sensor garment 10 may include performance, physiological, or other sensors 400 configured to detect heart rate (e.g., an ECG (electrocardiography) signal), respiration rate, body temperature, location, acceleration, distance, orientation, speed, direction, heading, oxygen levels, or hydration of a wearer. Such sensors 400 may include, for example, an electrode, a heart rate monitor (e.g., ECG sensor), a magnetometer, a respiratory sensor, a light sensor (e.g., to provide information about or interact with the environment of the wearer), a pressure sensor (e.g., to measure an impact or hit), a thermocouple, a GPS (global positioning system) sensor, an echolocation sensor, an RFID (radio-frequency identification) sensor, a beacon sensor, an accelerometer, a gyroscope, a compass, a biomechanic sensor, any other suitable sensor, or any combination thereof.

Figure 47:
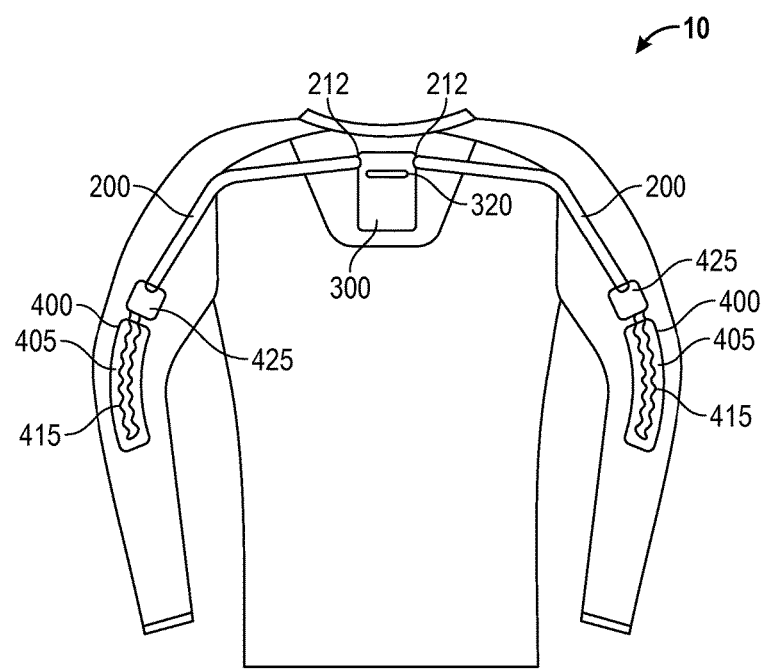
FIG. 47 is a perspective rear view of a garment according to an exemplary embodiment of the present invention.

A biomechanic sensor may, for example, include a stretch sensor 405 with a stretchable conductive element 415 (e.g., separate from or included in sensor garment 10 at an area configured to correspond to a portion of the body of a wearer that can have a large reflex range, for example, the elbow, knee, shoulder, or foot), as depicted in, for example, FIG. 47. Stretchable conductive element 415 may be, for example, stretchable wire (e.g., wire coiled around an elastic core), non-stretchable wire included in a stretch panel in, for example, a zigzag, sinusoidal, or loop pattern, or a conductive polymer or conductive fabric, as described further herein. Deformation of stretchable conductive element 415 may be sensed based on variations in the resistance of stretchable conductive element 415, and used to determine motion of the body of the wearer (e.g., occurrence, magnitude, speed, or direction of motion). In some exemplary embodiments, such variations in resistance are sensed at a resistance sensor/filter 425 located adjacent and directly attached to stretchable conductive element 415, and are communicated to monitor device 500 via harness 200.

Further examples of exemplary sensors 400 and their potential uses can be found in commonly owned U.S. patent application Ser. No. 13/077,494, filed Mar. 31, 2011, entitled "Group Performance Monitoring System and Method," the disclosure of which is hereby incorporated in its entirety by reference thereto. In some exemplary embodiments, sensors 400 may form a part of sensor garment 10, and may be integrated within or attached to textile layer 100. In some exemplary embodiments, sensors 400 may be separate from and adapted to be coupled to sensor garment 10. In some exemplary embodiments, sensor 400 may be a receiver, which can act as an antenna 450 to receive a signal from a remote sensor or transmitter. For example, in such an embodiment, the receiver may be configured to receive a signal from a core temperature sensor swallowed by a wearer, and may be positioned to correspond to the center of the back of the wearer, off of the spine, as shown, for example, in FIG. 43. In some exemplary embodiments, sensor 400 may include or be coupled to a speaker and/or microphone 460, as depicted in, for example, FIG. 38. Speaker and/or microphone 460 may transmit or receive audio information to or from a remote device and monitor device 500. Speaker and/or microphone 460 may enable communication between a wearer of sensor garment 10 and a person remote from the wearer.

Antenna 450 may be separate from or integrated within monitor device 500. In embodiments where antenna 450 is separate from monitor device 500, antenna 450 may be coupled to textile layer 100. Antenna 450 may be configured to facilitate communication between monitor device 200 and a remote sensor or transmitter, by, for example, wirelessly sending and receiving signals between these elements. Antenna 450 may be formed of, for example, coiled or wrapped conductive wires, conductive fabric, conductive adhesive, conductive thread, conductive polymer, or silver ink printed on plastic. In some exemplary embodiments, antenna 450 is coupled to textile layer 100 (or any portion of sensor garment 10) by a retention element, which may be, for example, a retention element similar device retention element 300, described herein. In some exemplary embodiments, antenna 450 is coupled to textile layer 100 (or any portion of sensor garment 10) by being sewn thereto, or laminated, glued, ultrasonically bonded, or printed thereon. In some exemplary embodiments, padding is included proximate to antenna 450, which may protect antenna 450 and reduce discomfort of a wearer of sensor garment 10. The padding may be any suitable padding, such as, for example, the material of spacer element 340 (described herein), or a polymer (e.g., soft silicone).

Depending on the type of sensor 400, sensor 400 may be positioned within sensor garment 10 to be configured to be in contact with the skin of a wearer of sensor garment 10. In some exemplary embodiments, at least a portion of sensor 400 is uncoupled from the motion of the remaining portion of sensor garment 10 relative to the body of the wearer. As a wearer's body moves during activity, this in turn causes all or a portion of the sensor garment 10 to move. In order to minimize undesirable motion of a portion of sensor 400 relative to the body of the wearer, the portion of sensor 400 may be fixed to the body of the wearer, and coupled to harness 200 using a technique that allows relative motion between harness 200 and the portion of sensor 400, as described below. Because at least a portion of sensor 400 is fixed to the body of the wearer, as opposed to textile layer 100, the portion of sensor 400 may not be subjected to the motion of the garment. This can help maintain reliable and consistent skin contact and positioning relative to the wearer. For example, in some exemplary embodiments, sensors 400 are coupled to the remaining portion of sensor garment 10 (e.g., harness 200) by dangling therefrom. A dangling sensor 400 may have some slack in its connection to harness 200 (e.g., an extended wire connection), thereby allowing for relative motion between sensor 400 and harness 200. A dangling sensor 400 may connect to the skin of a wearer via, for example, suction, tape, or an adhesive substance. In this manner, in some embodiments a portion of sensor 400 may be fixed relative to the motion of sensor garment 10 (and move relative to the body of the wearer), and a portion of sensor 400 may move relative to the sensor garment 10 (and be substantially fixed relative to the body of the wearer).

In some exemplary embodiments, sensors 400 are incorporated into a band 420, as depicted, for example, in FIGS. 24, 25, 40, and 41, which may be elastic and may be configured to surround the chest or other anatomical feature of a wearer. In the exemplary embodiments of FIGS. 24, 25, 40, and 41, sensor garment 10 is shown inside-out, for ease of depiction. In some exemplary embodiments, such a band 420 may be attached to textile layer 100 (e.g., sensors 400 may be attached to an inner support layer (e.g., band 420) of sensor garment 10, which may be integrated with textile layer 100, as depicted, for example, in FIG. 40, or which may be attached to textile layer 100 at discrete points, as depicted, for example, in FIG. 41). In some exemplary embodiments, such a band 420 may be independent from textile layer 100 (e.g., sensors 400 may be integrated into a bra-like garment that can be worn underneath textile layer 100, and the sensors thereof may be configured to couple to harness 400).

Depending on a variety of factors, including type of sensor, type of garment, aesthetics, and manufacturing considerations, sensors 400 may be positioned at a variety of locations relative to device retention element 300, and may be positioned at any suitable location on or in textile layer 100 (e.g., on areas of textile layer configured to correspond to the torso, back, sides, arms, or neck of the wearer), or separate therefrom. In some exemplary embodiments, sensor garment 10 includes harness 200 to connect sensors 400 to device retention element 300 and to monitor device 500, when monitor device 500 is retained by device retention element 300.

Harness 200 may include, as shown in FIG. 1, for example, electrically conductive elements 210, capable of communicating data electronically, and a harness guide portion 220. Conductive elements 210 may include one or a plurality of termination points, as shown in, for example, FIGS. 3 and 4. For example, conductive elements 210 may include a first termination point 212, a second termination point 214, and a third termination point 216. The configuration of these termination points can be varied, as will be described below. Harness guide portion 220 may include a plurality of layers, as shown in, for example, FIG. 17. For example, harness guide portion may include a first layer 222, a second layer 224, and a fabric layer 226, which will be discussed below. In some exemplary embodiments, conductive elements 210 are disposed between layers of harness guide portion 220.

In some exemplary embodiments, harness 200 may be disposed integrally with or on a surface of textile layer 100 of garment 10. In the exemplary embodiment of FIG. 1, sensor garment 10 is shown inside-out, for ease of depiction. Thus, in normal use, harness 200 of the exemplary embodiment of FIG. 1 would be positioned on an interior surface of textile layer 100 of sensor garment 10. In some exemplary embodiments, harness 200 may be positioned on or adjacent an interior surface of textile layer 100, positioned on or adjacent an exterior surface of textile layer 100, or integrated within textile layer 100. Harness 200 may couple to textile layer 100 by any suitable technique, including, for example, adhesive, stitching, welding, or lamination. Throughout the figures, sensor garment 10 can be interpreted as being depicted inside-out or inside-in.

Figure 29:
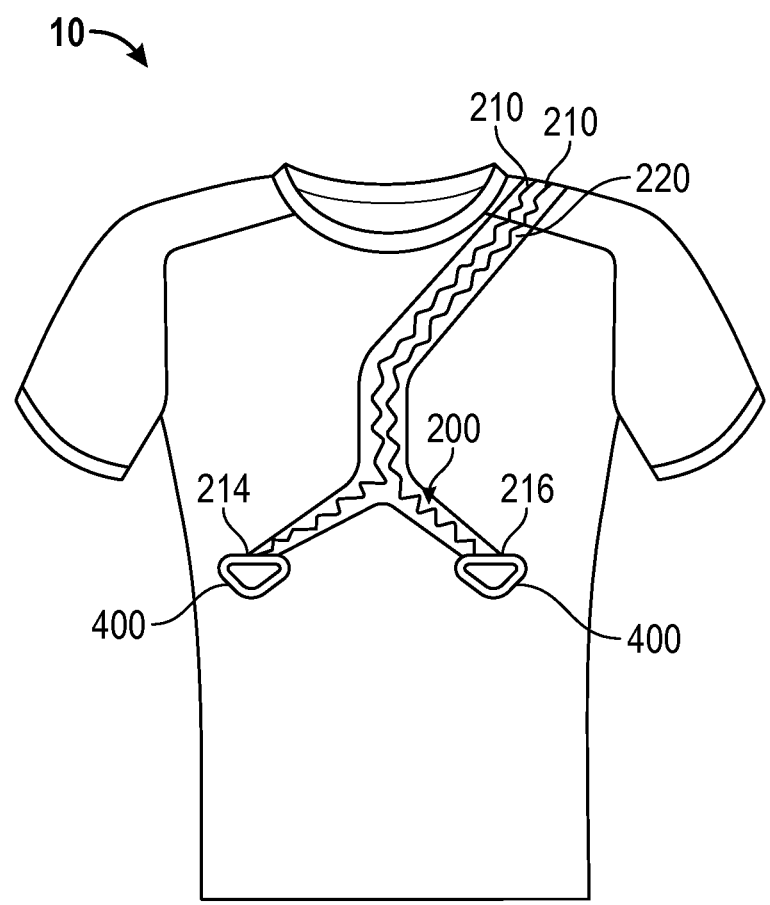
FIG. 29 is a perspective front view of a garment, shown inside-out, according to an exemplary embodiment of the present invention.

Conductive elements 210 may be configured to connect to sensors 400, as depicted in, for example, FIG. 29, and to monitor device 500, and may be configured to transmit data from sensors 400 to monitor device 500. To accomplish this, conductive elements 210 may include termination points corresponding to sensors 400 and monitor device 500. As shown in, for example, FIGS. 3, 4, and 34, conductive elements 210 may include a first termination point 212, configured to connect to monitor device 500 (see, e.g., FIGS. 4, 6, 8, and 12), a second termination point 214 to connect to a sensor 400, and a third termination point 216 to connect to another sensor 400. Each termination point may include a single or multiple terminal connections, depending on the configuration of conductive elements 210 at the termination point. In the case where a termination point has multiple terminal connections, these connections may be labeled to facilitate proper connection with additional components. For example, a termination point configured to connect to monitor device 500 may include two terminal connections, labeled "Left" and "Right", indicating that they correspond to sensors positioned in the left and right of sensor garment 10, respectively. Conductive elements 210 of harness 200 may include any suitable number and arrangement of termination points to suit an arrangement of sensors 400 and monitor device 500.

Figure 3:
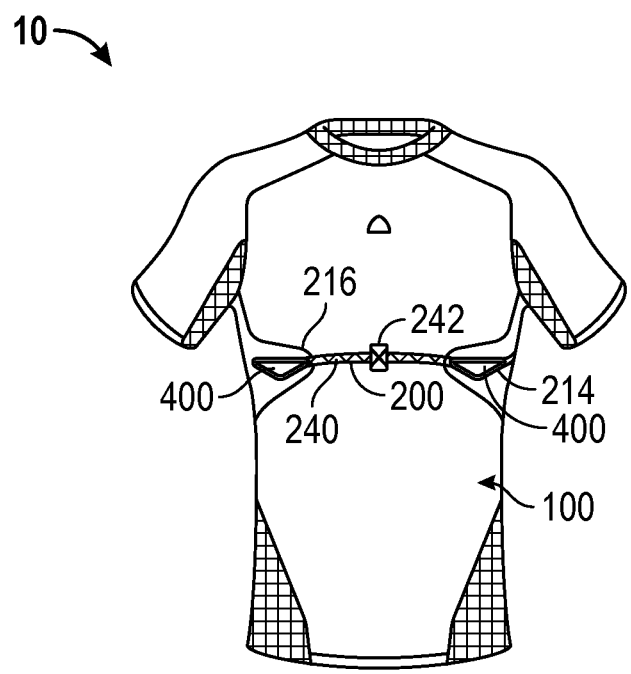
FIG. 3 is a perspective front view of a garment according to an exemplary embodiment of the present invention.
Figure 4:
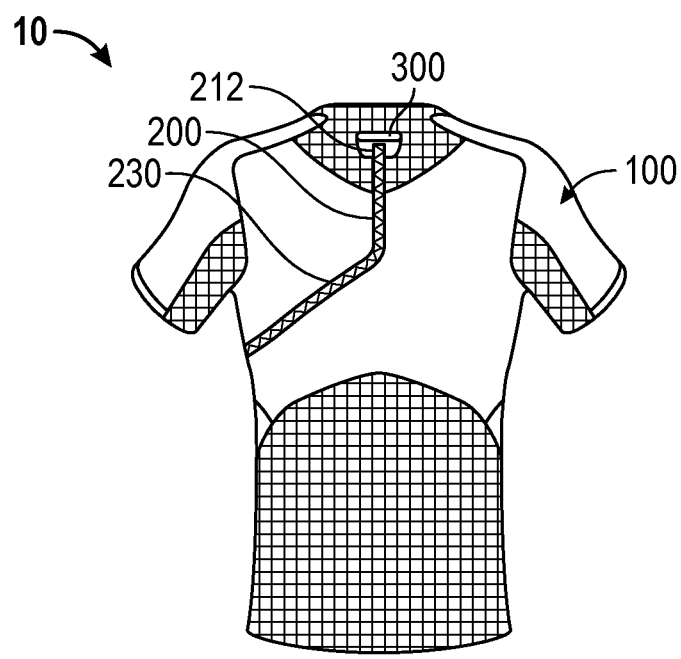
FIG. 4 is a perspective rear view of the garment of FIG. 3 according to an exemplary embodiment of the present invention.
Figure 5:
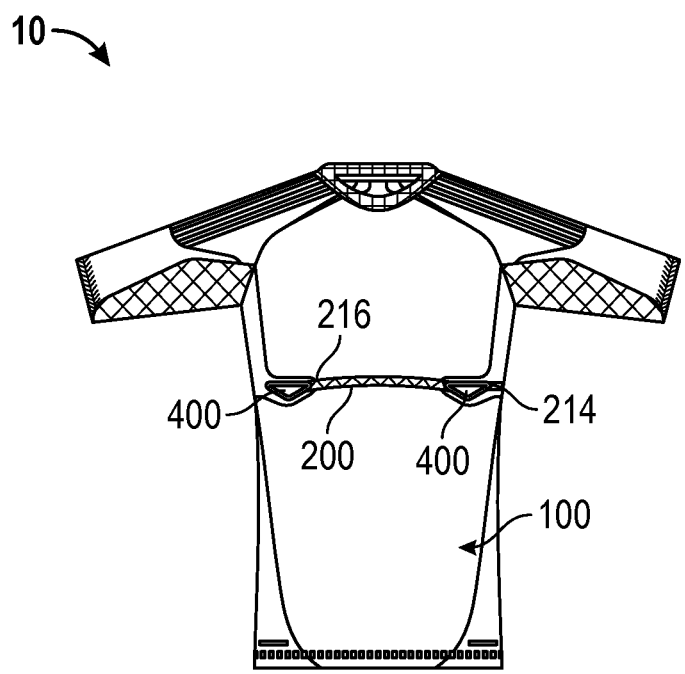
FIG. 5 is a perspective front view of a garment according to an exemplary embodiment of the present invention.
Figure 6:
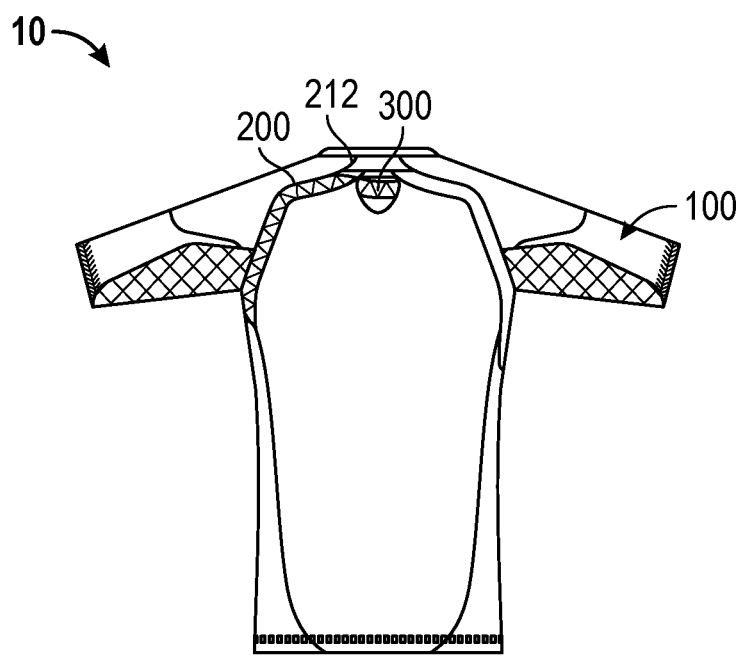
FIG. 6 is a perspective rear view of the garment of FIG. 5 according to an exemplary embodiment of the present invention.
Figure 7:
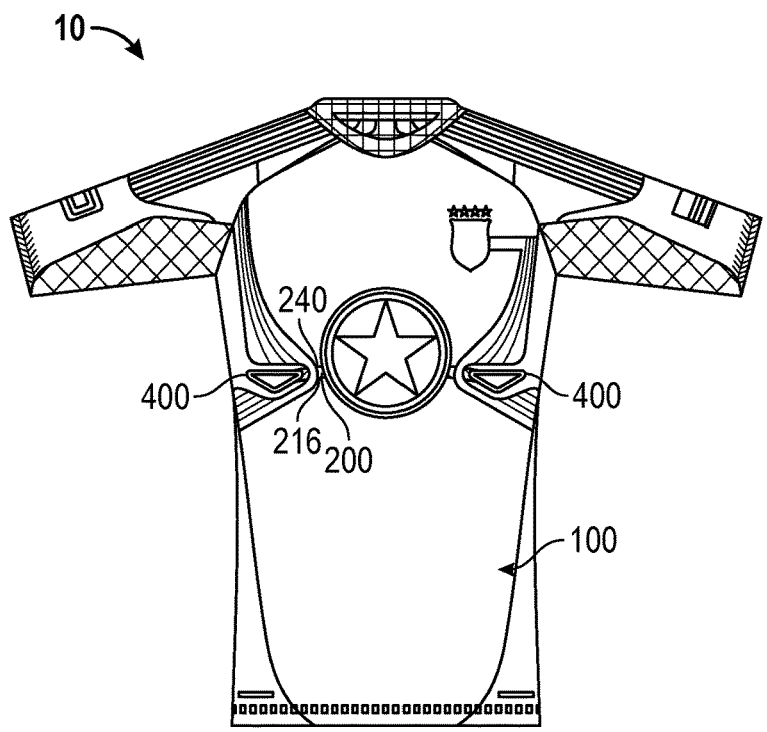
FIG. 7 is a perspective front view of a garment according to an exemplary embodiment of the present invention.
Figure 8:
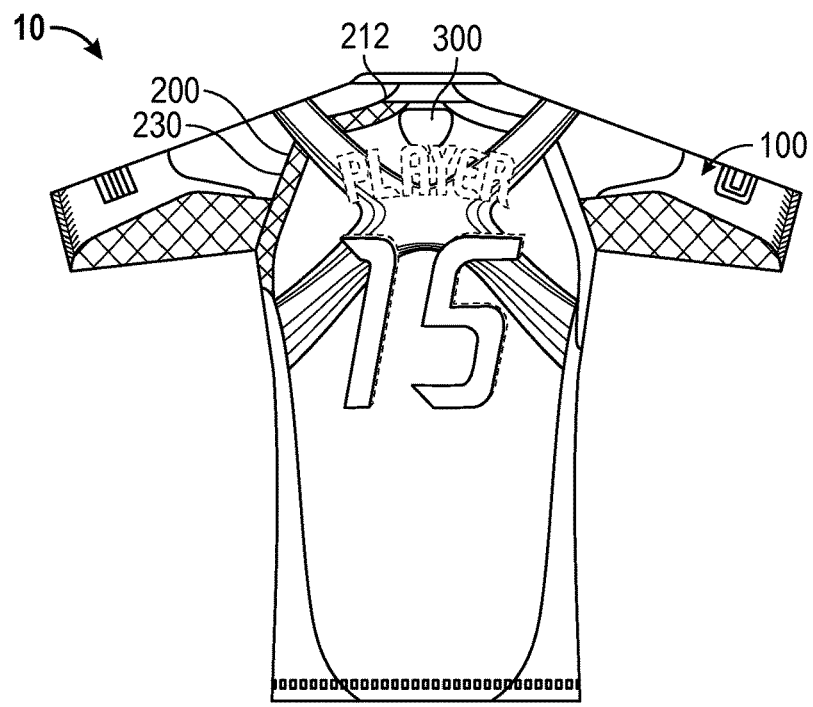
FIG. 8 is a perspective rear view of the garment of FIG. 7 according to an exemplary embodiment of the present invention.

Guide portion 220 of harness 200 may guide conductive elements 210 between termination points, as depicted in the exemplary embodiments of FIGS. 1, 3, and 4, for example. In some exemplary embodiments, guide portion 220 is formed of a first layer 222 and a second layer 224, wherein the first layer 222 and second layer 224 are configured to be coupled together with conductive elements 210 therebetween, as depicted in the exemplary embodiment of FIG. 17, for example. In some exemplary embodiments, one or both of first layer 222 and second layer 224 is an adhesive layer.

In some exemplary embodiments, harness 200 includes a fabric layer 226 coupled to guide portion 220. Fabric layer 226 may be elastic and may be positioned to correspond to an interior of sensor garment 10, thereby reducing discomfort of a wearer due to harness 200.

In some exemplary embodiments, as depicted in, for example, FIGS. 3 and 4, harness 200 includes a first harness portion 230, which is fixed directly to textile layer 100, and a second harness portion 240, which is at least partially free from fixation to textile layer 100. Second harness portion 240 may be referred to as a "bridge". In some exemplary embodiments the motion of second harness portion 240 relative to textile layer 100 may be constrained by a loop 242 attached to textile layer 100 and looping around second harness portion 240. Second harness portion 240 may be particularly useful to enable communication between sensors 400 and monitor device 500 across areas of sensor garment 10 that are not conducive to direct fixation of harness 200. For example, in some exemplary embodiments, harness 200 may be best suited for direct fixation to textile layer 100 in areas where textile layer 100 is elastic. In order to maintain connection between elements of sensor garment 10 that are positioned on different sides of an inflexible portion of sensor garment 10 harness 200 may include, for example, second harness portion 240 to bridge the inflexible portion of sensor garment 10, thereby connecting the elements of sensor garment 10 without requiring direct fixation to inflexible areas of sensor garment 10. Textile layer 100 of sensor garment 10 may include panels of flexible and inflexible material in order to achieve a desired fit or aesthetic, or to provide for undistorted graphics, such as, for example, team or sponsor logos or player numbers, in the case of a team jersey.

The routing of harness 200 may be configured to suit a variety of requirements or desires. For example, in some exemplary embodiments, harness 200 may be routed to only cover areas of sensor garment 10 that do not or will not include graphics or print, so as not to interfere with the aesthetics or production of such graphics or print.

In some exemplary embodiments, second harness portion 240 may "bridge" over such graphics or print. In some exemplary embodiments, harness 200 may be routed so as not to cross or interfere with seams of sensor garment 10, in order to, for example, simplify manufacturing and to maintain durability of sensor garment 10. In some exemplary embodiments, harness 200 may be incorporated with or otherwise extend along seams of sensor garment 10.

In some exemplary embodiments, as depicted in, for example, FIGS. 3, 4, 11, and 12, harness 200 extends from first termination point 212, configured to be positioned at the upper back of a wearer, down the back and around one side of sensor garment 10 to second termination point 214, configured to be positioned at one side of the wearer, across the front of sensor garment 10 to third termination point 216, configured to be positioned at the other side of the wearer.

In some exemplary embodiments, as depicted in, for example, FIGS. 5-8, harness 200 extends from first termination point 212, configured to be positioned at the upper back of a wearer, along the back shoulder, and around one side of sensor garment 10 to second termination point 214, configured to be positioned at one side of the wearer, across the front of sensor garment 10 to third termination point 216, configured to be positioned at the other side of the wearer.

Figure 24:
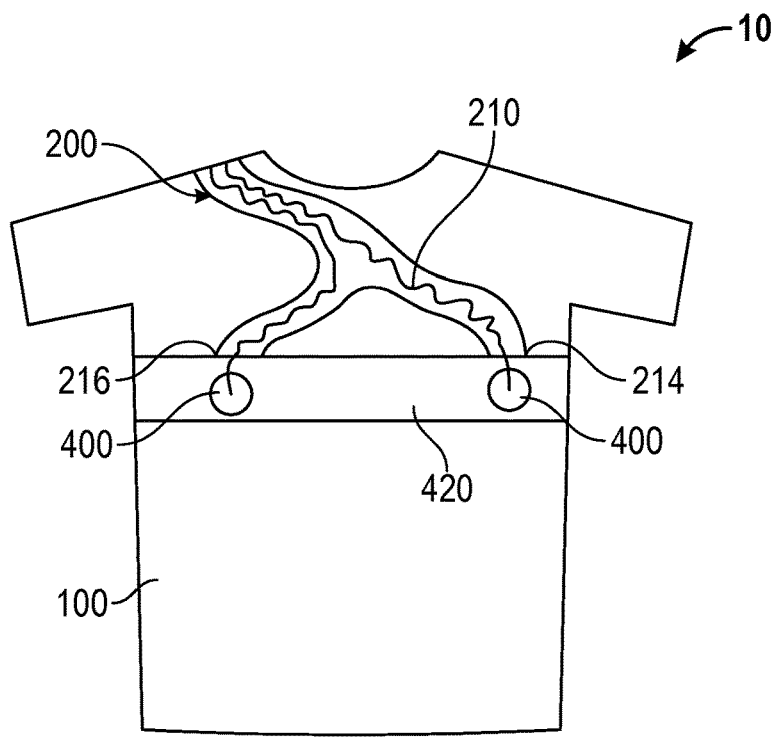
FIG. 24 is a perspective front view of a garment, shown inside-out, according to an exemplary embodiment of the present invention.
Figure 25:
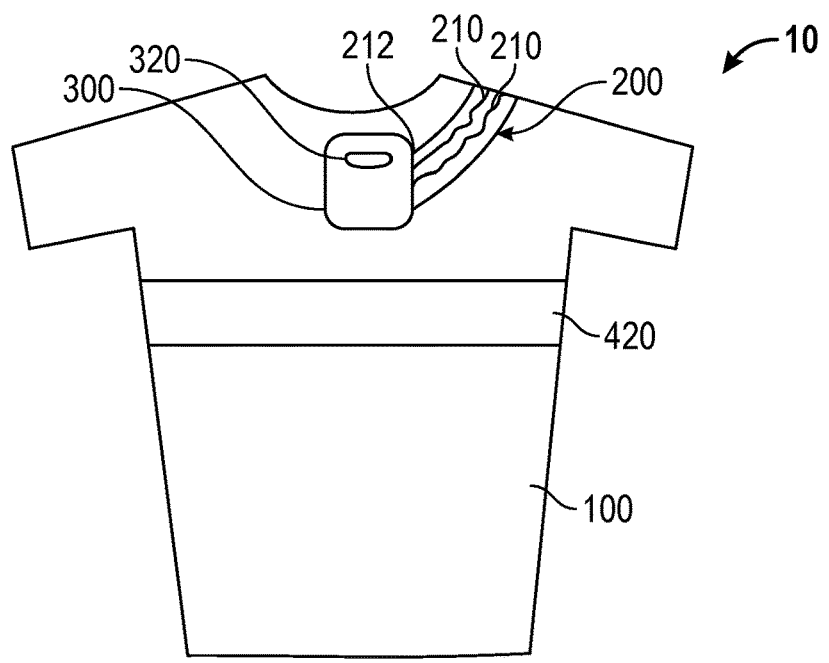
FIG. 25 is a perspective rear view of the garment of FIG. 24 according to an exemplary embodiment of the present invention.

In some exemplary embodiments, as depicted in, for example, FIGS. 1, 24, and 25 harness 200 extends from first termination point 212, configured to be positioned at the upper back of a wearer, over a shoulder area of sensor garment 10 to the front of sensor garment 10, and splits into prongs, leading to each of termination points 214 and 216, configured to be positioned at the sides of the wearer.

In some exemplary embodiments, as depicted in, for example, FIGS. 45 and 46, harness 200 extends from first termination point 212, configured to be positioned at the upper back of a wearer, down the back, where it splits into two portions that extend around opposing sides of sensor garment 10, one portion extending to second termination point 214, configured to be positioned at one side of the wearer, and the other portion extending to a third termination point 216, configured to be positioned at the opposite side of the wearer.

Figure 31:
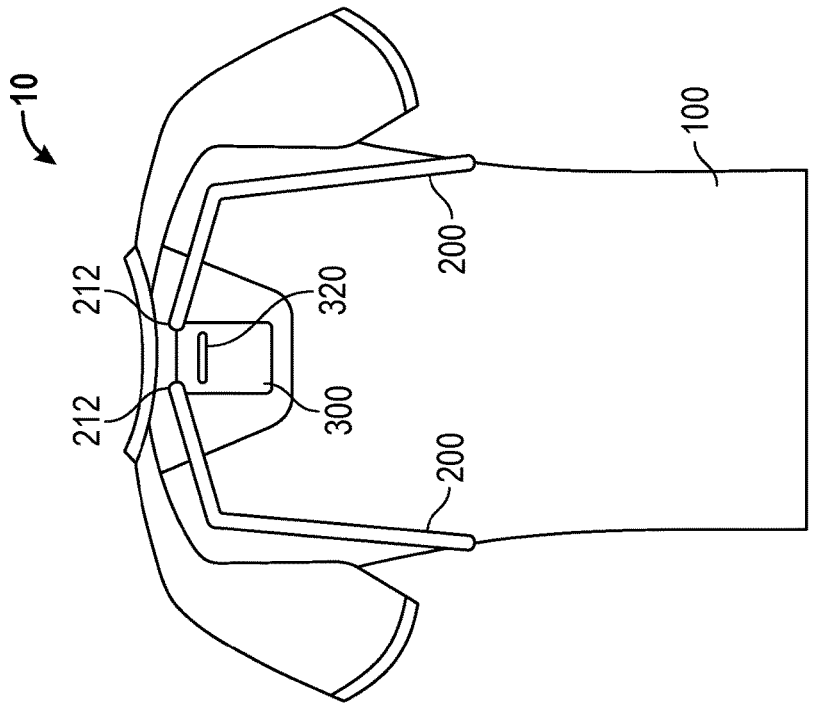
FIG. 31 is a perspective rear view of the garment of FIG. 30 according to an exemplary embodiment of the present invention.
Figure 30:
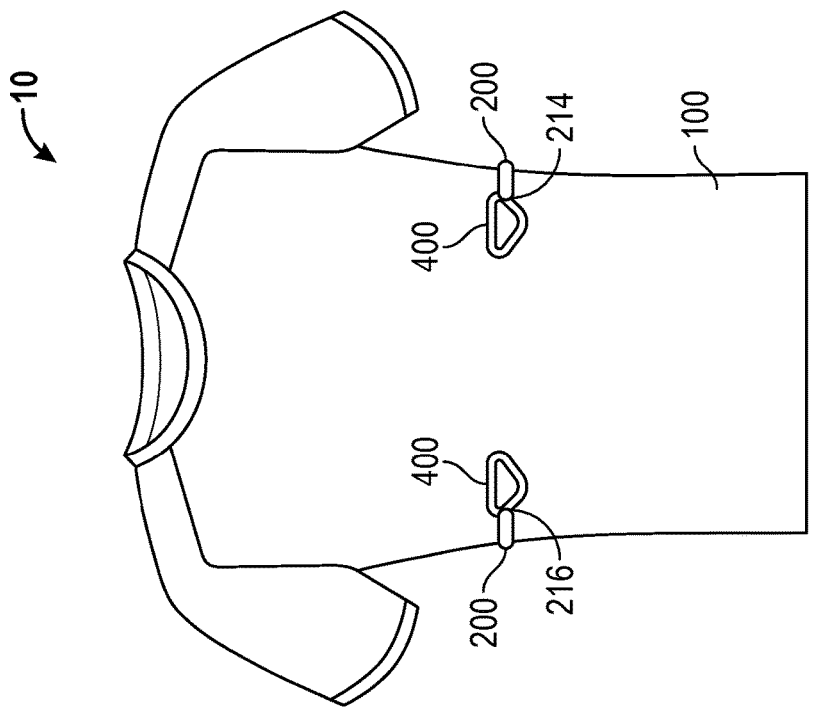
FIG. 30 is a perspective front view of a garment according to an exemplary embodiment of the present invention.

In some exemplary embodiments, as depicted in, for example, FIGS. 30 and 31, harness 200 extends, in two portions, from each of two first termination points 212, located at left and right sides of device retention element 300. Device retention element 300 may be positioned at an upper back area of sensor garment 10. One portion of harness 200 may extend along the back left shoulder, under the left arm, to second termination point 214, and the other portion may extend along the back right shoulder, under the right arm, to third termination point 216.

In some exemplary embodiments, as depicted in, for example, FIG. 47, harness 200 extends, in two portions, from each of two first termination points 212, located at left and right sides of device retention element 300. Device retention element 300 may be positioned at an upper back area of sensor garment 10. One portion of harness 200 may extend along the back left shoulder, along the left arm, to second termination point 214 located at a left elbow area of sensor garment 10, and the other portion may extend along the back right shoulder, along the right arm, to third termination point 216 located at a right elbow area of sensor garment 10.

Figure 35:
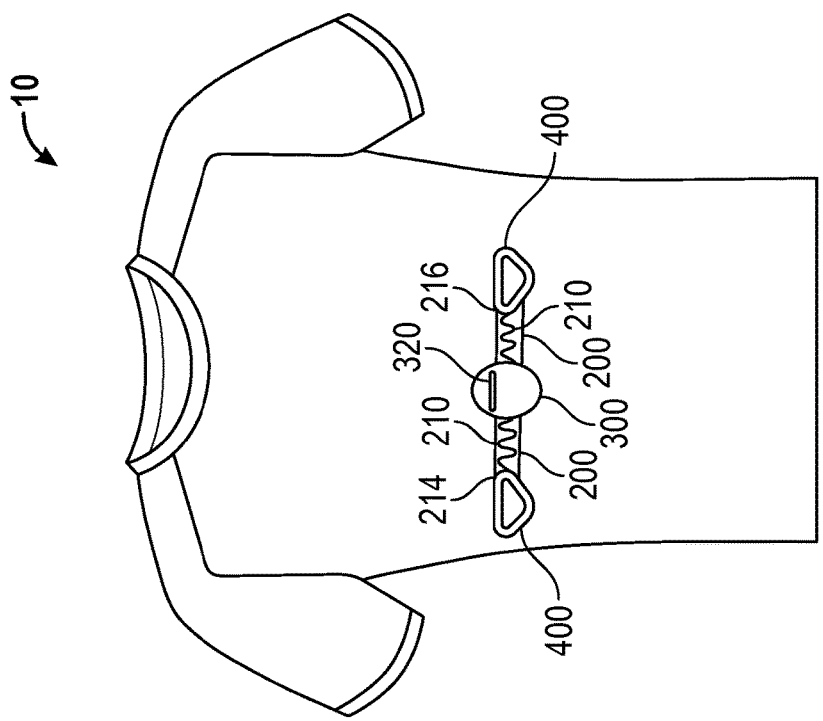
FIG. 35 is a perspective front view of a garment according to an exemplary embodiment of the present invention.

In some exemplary embodiments, as depicted in, for example, FIG. 35, harness 200 extends, in two portions, from each of two first termination points 212, located at left and right sides of device retention element 300. Device retention element 300 may be positioned at a central front area of sensor garment 10, between sensors 400. One portion of harness 200 may extend left to second termination point 214, and the other portion may extend right to third termination point 216.

Figure 36:
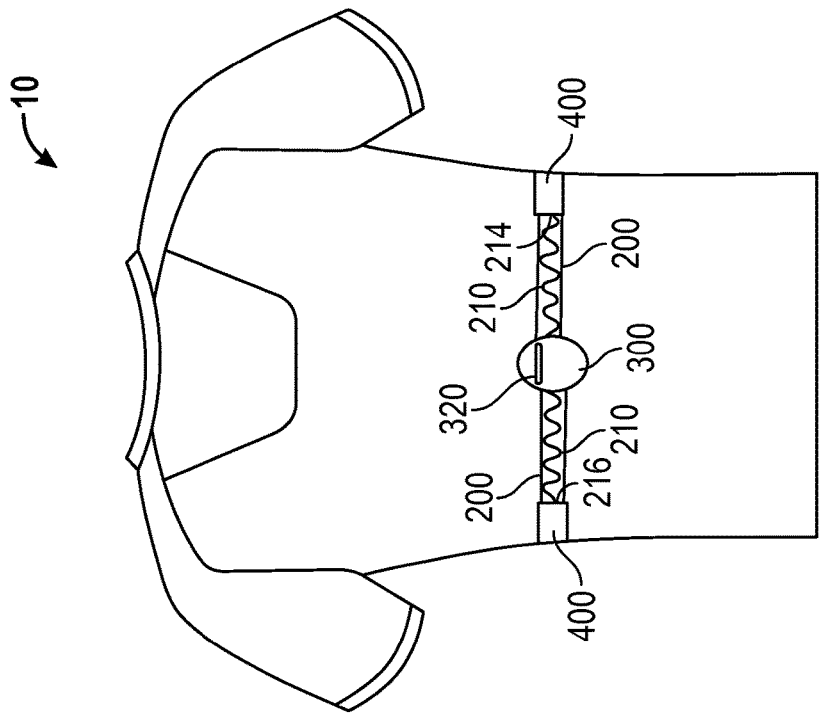
FIG. 36 is a perspective rear view of a garment according to an exemplary embodiment of the present invention.

In some exemplary embodiments, as depicted in, for example, FIG. 36, harness 200 extends, in two portions, from each of two first termination points 212, located at left and right sides of device retention element 300. Device retention element 300 may be positioned at a central back area of sensor garment 10, between sensors 400. One portion of harness 200 may extend right to second termination point 214, and the other portion may extend left to third termination point 216.

Figure 37:
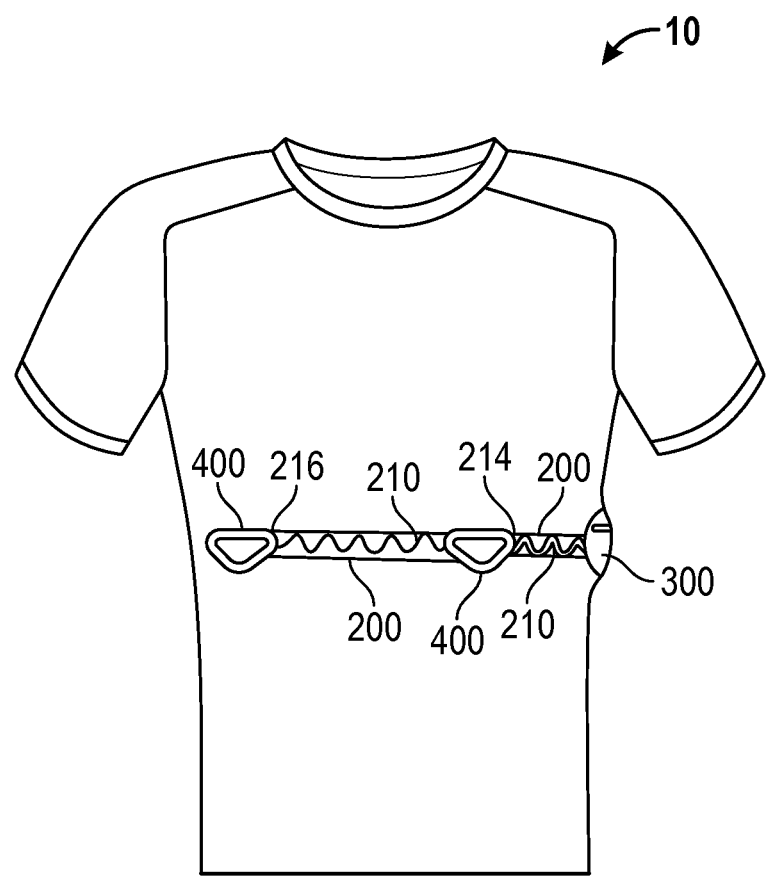
FIG. 37 is a perspective front view of a garment according to an exemplary embodiment of the present invention.

In some exemplary embodiments, as depicted in, for example, FIG. 37, harness 200 extends from first termination point 212, located at device retention element 300. Device retention element may be positioned at a side area of sensor garment 10. Harness 200 may extend to second termination point 214 at one side of the front of sensor garment 10, and from second termination point 214 across the front of sensor garment 10 to third termination point 216 at the other side of the front of sensor garment 10.

The shape and routing of harness 200 may be varied to suit a wide variety of particular requirements or desires, including various positions of monitor device 500 or sensors 400. For example, rather than being routed to sensors 400 at a wearer's front or sides, harness 200 may be routed to a chest or back area of the wearer, to correspond to sensors 400 positioned at the chest or back of the wearer (e.g., a heart rate sensor configured to be positioned at the middle of the chest of a wearer). In some exemplary embodiments, for example, those depicted in FIGS. 1, 5, and 30, sensors 400 are positioned to correspond to side areas of a wearer located at the front of the wearer. In some exemplary embodiments, for example, those depicted in FIGS. 32 and 33, sensors 400 are positioned at extreme side areas of sensor garment 10. In some exemplary embodiments, for example, that depicted in FIG. 36, sensors 400 are positioned at side areas at a rear of sensor garment 10.

Sensors 400 may have various shapes and sizes, to suit a variety of requirements or desires. In some exemplary embodiments, operation of some or all sensors 400 may benefit from contact with the skin of a wearer. In such an exemplary embodiment, a sensor 400 may be shaped and sized to correspond to the anatomical shape and size of a particular area of a wearer's skin that it is intended to be in contact with. In some exemplary embodiments, to optimize skin contact, sensors 400 may be brush-like sensors (e.g., a sensor having a plurality of contact elements extending therefrom, to provide a plurality of potential contact points for sensor 400), pillowed (e.g., a sensor supported by a backing material between the sensor and textile layer 100, where the backing material causes the sensor to tend to extend out from the textile layer against the wearer's skin, and may be, for example, the material of spacer element 340 or the lofty polyester fiberfill commonly used in sleeping pillows), or may include sticky areas (e.g., adhesive around a periphery of sensor 400). In some exemplary embodiments, to optimize skin contact of sensors 400, an inner surface of textile layer 100 may include sticky areas around sensors 400 attached thereto, or may include areas around sensors 400 configured to naturally adhere to the skin of a wearer (e.g., silicone panels). In some exemplary embodiments, sensor garment 10 is configured to maintain contact between sensors 400 and the skin of a wearer through a tight fit of sensor garment 10 (e.g., a compression shirt). In some exemplary embodiments, some or all sensors 400 may have no need for contact with the skin of a wearer, and may be positioned so as not to contact the skin.

Harness 200 may be subject to forces, during use, that cause it to deform or otherwise tend to stretch. Harness 200 may be made of elastic materials, so as to be stretchable and able to elastically accommodate such forces. For example, first layer 222, second layer 224, and fabric layer 226 may each be composed of elastic materials. Further, in some exemplary embodiments, conductive elements 210 may be elastic. Harness 200, according to exemplary embodiments, exhibits stretchability, durability, and stress release properties. As will be apparent to one of skill in the art, these characteristics can be adjusted and optimized for a variety of requirements or applications. In some exemplary embodiments, harness 200 has elasticity substantially equivalent to that of textile layer 100. In some exemplary embodiments, harness 200 has elasticity greater than that of textile layer 100. In some exemplary embodiments, harness 200 has elasticity less than that of textile layer 100. In some exemplary embodiments, harness 200 has sufficient elasticity to conform to the body of a wearer, thereby promoting contact of sensors 400 with the body of the wearer.

In some exemplary embodiments, harness 200 has sufficient elasticity to withstand stretching incident to a wearer's donning and doffing of sensor garment 10. In some exemplary embodiments, harness 200 is configured to stretch to 20-100% of its non-stretched length without being permanently deformed in any direction. In some exemplary embodiments, different portions of harness 200 are configured to stretch to different proportions of their non-stretched lengths without being permanently deformed. For example, portions of harness 200 positioned around a neckline of sensor garment 10 may be configured to stretch 20-30% of their non-stretched lengths, while portions such as the neck of a Y-shape of a harness 200, or portions of harness 200 positioned at the chest or mid-torso areas of sensor garment 10 may be configured to stretch 80-100%. In some exemplary embodiments, portions of harness 200 may be configured to stretch more in a cross-body direction than in a vertical direction, and vice versa.

In some exemplary embodiments, textile layer 100 has sufficient elasticity to conform to the body of a wearer, thereby promoting contact of sensors 400 with the body of the wearer. In some exemplary embodiments, textile layer 100 includes portions with greater elasticity than other portions of textile layer 100, where the portions with greater elasticity may correspond to areas where harness 200 is coupled to textile layer 100. In some exemplary embodiments, stretch and elasticity characteristics of sensor garment 10 (in particular conductive elements 210, adhesive first layer 222, second layer 224, fabric layer 226, and/or textile layer 100) are configured to facilitate durability, freedom of movement, and donning and doffing of sensor garment 10.

Figure 17:
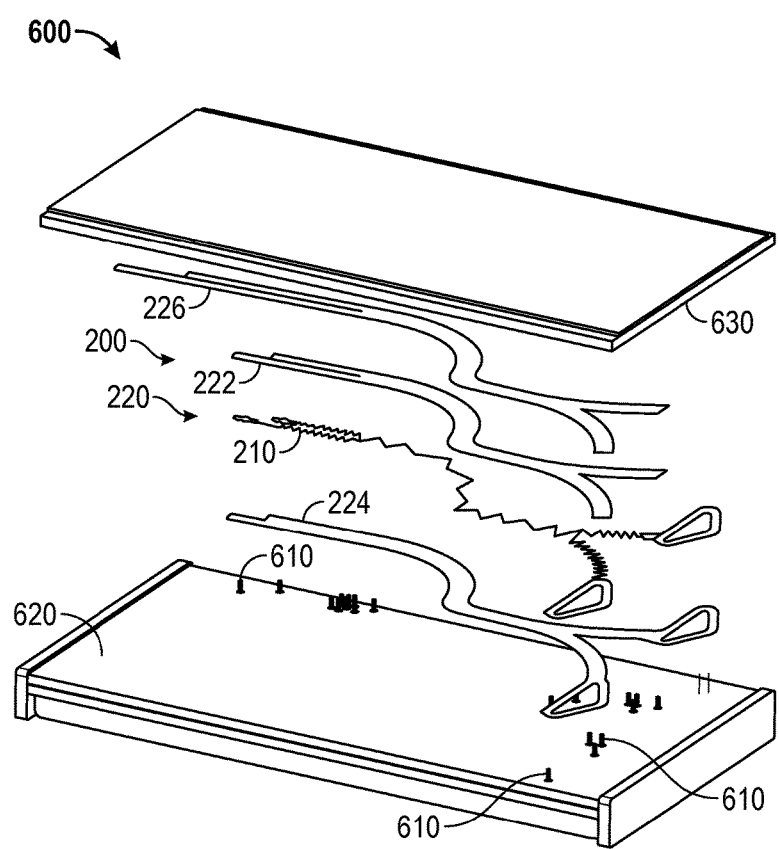
FIG. 17 is a perspective view of a harness manufacturing technique according to an exemplary embodiment of the present invention.
Figure 34:
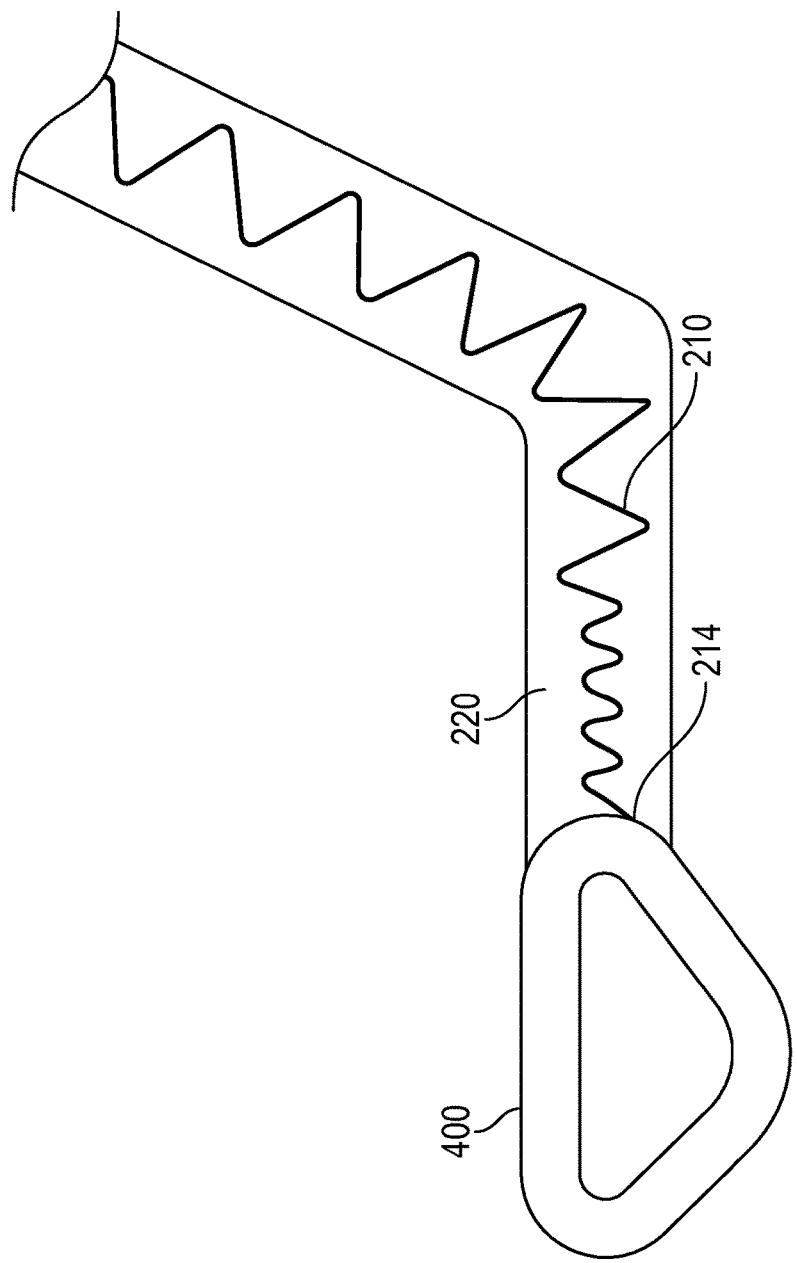
FIG. 34 is an enlarged view of a sensor according to an exemplary embodiment of the present invention.

Conductive elements 210 may include conductive wire or yarn, for example, multi-strand, individually insulated, high flexibility micro-wire (e.g., silver coated nylon or composite material with an elastic core encircled with conductive material), conductive silver yarn, or insulated conductive wire, arranged in a zigzag, loop, meander, or sinusoidal pattern, as shown in, for example, FIGS. 1, 17, and 34. To increase flexibility, the pattern may adopt a lesser magnitude or greater frequency (of, for example, peaks or loops per unit of distance) as conductive elements 210 approach termination points, or anywhere else greater stretchability in harness 200 may be required or desired, and may maintain a greater magnitude or frequency in other areas of harness 200, to maintain durability. In one embodiment, as shown in, for example, FIGS. 17 and 34, the sinusoidal pattern of conductive elements 210 may exhibit greater frequency and lesser magnitude near the ends of conductive elements 210, and lesser frequency and greater magnitude along an intermediate portion of conductive elements 210. Portions of greater frequency and lesser magnitude may correspond to portions of harness 200 configured to be coupled to monitor device 500 or sensors 400, or in areas of harness routing that receive greatest stress in donning, doffing, or wearing. Such portions may benefit from increased stretchability and strain relief provided thereby.

Sensor garment 10 may move and stretch during activity of a wearer, and the connection between conductive element 210 and sensors 400 or monitor device 500 may be stressed. Increased flexibility and elasticity in these areas may help minimize such stress. Portions of lesser frequency and greater magnitude may correspond to portions of harness 200 configured to be positioned under or over an arm of the wearer, where flexibility and maintaining connection to additional elements is less important. In one exemplary embodiment, shown in FIG. 1, the sinusoidal pattern of conductive elements 210 may transition to a straight line as conductive elements 210 approach second termination point 214 and third termination point 216. The nature of the pattern of conductive elements 210 can be varied to suit a variety of requirements or desires. Some level of flexibility throughout harness 200 may be beneficial, however, in order to reduce stress and fatigue on conductive elements 210, thereby increasing the useful life of harness 200.

Figure 40:
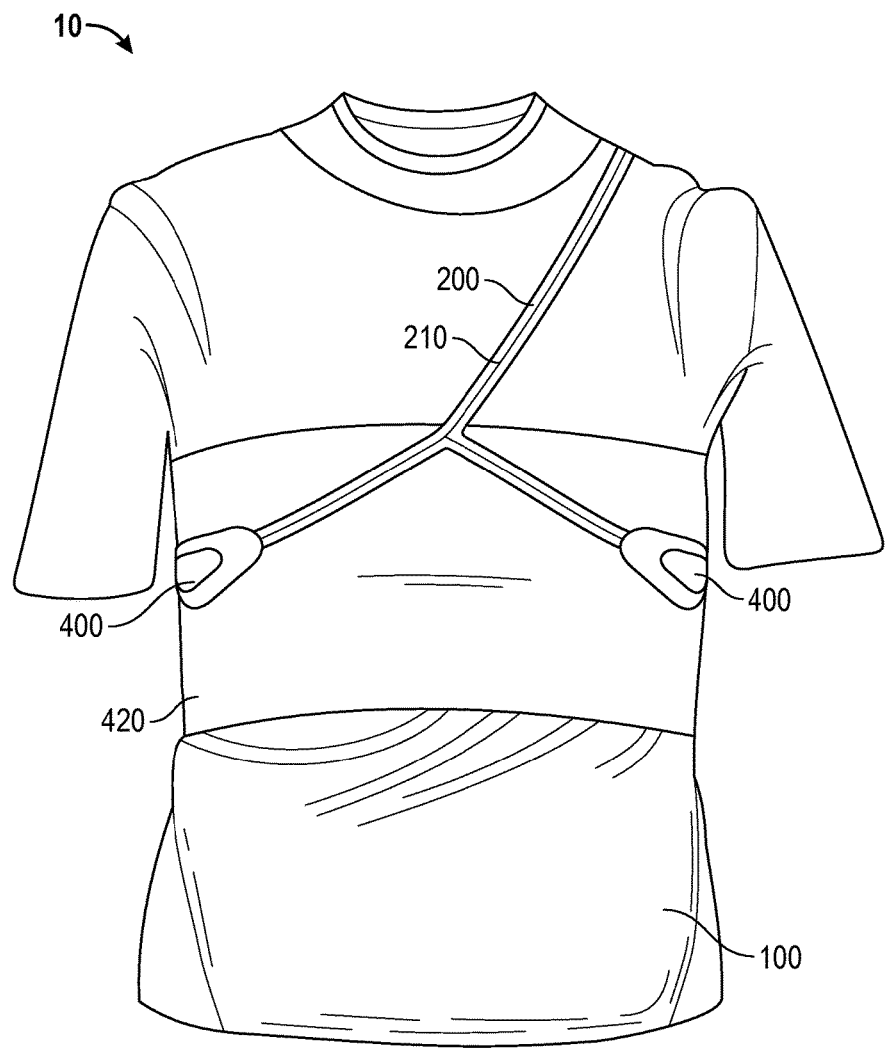
FIG. 40 is a perspective front view of a garment, shown inside-out, according to an exemplary embodiment of the present invention.
Figure 41:
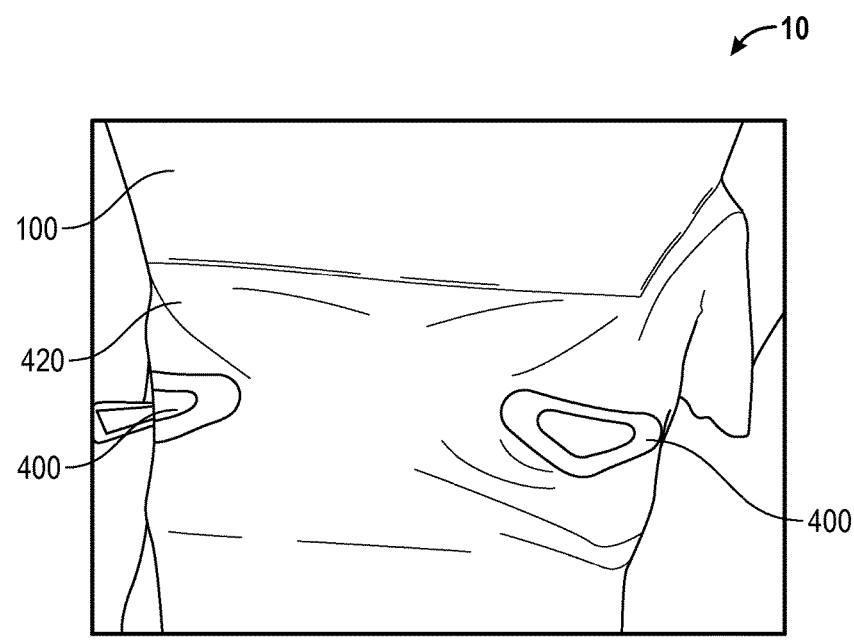
FIG. 41 is a perspective front view of a garment, shown inside-out, according to an exemplary embodiment of the present invention.
Figure 42:
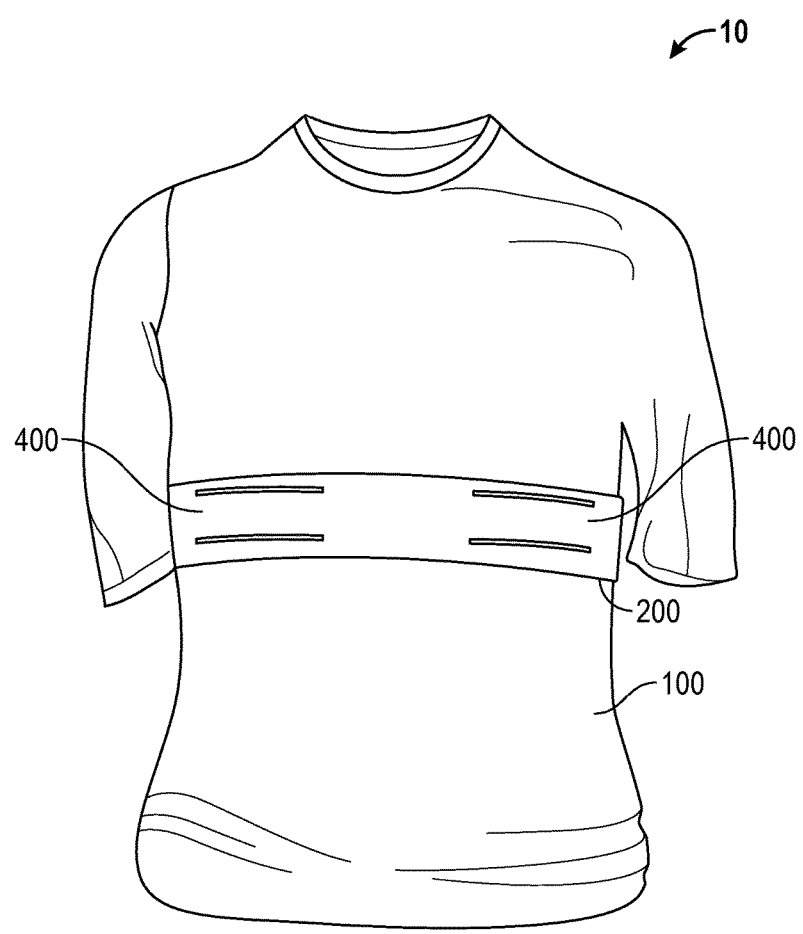
FIG. 42 is a perspective front view of a garment, shown inside-out, according to an exemplary embodiment of the present invention.
Figure 43:
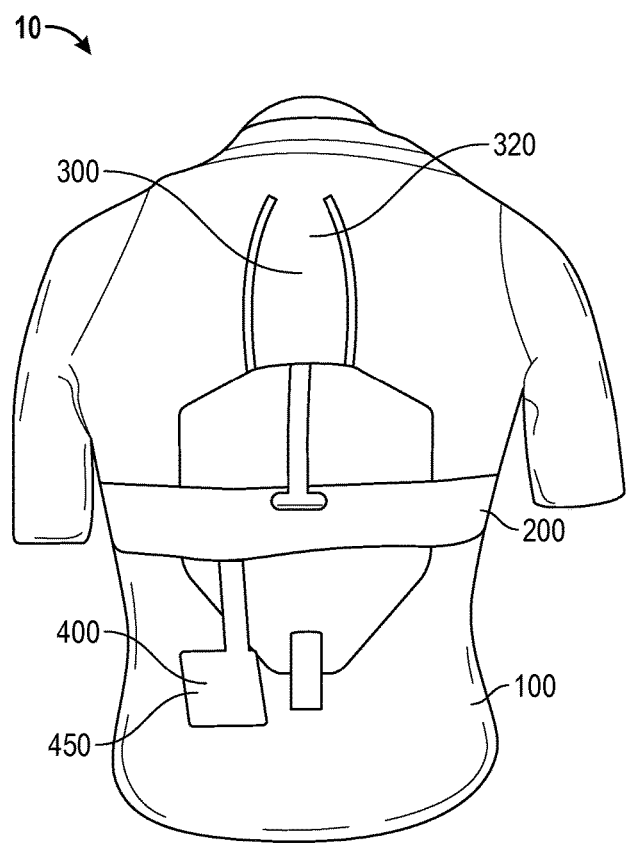
FIG. 43 is a perspective rear view of the garment of FIG. 42, shown inside-out, according to an exemplary embodiment of the present invention.

Conductive elements 210 may be patterned between connected first layer 222 and second layer 224. Harness 200 may include two or more conductive elements 210 that are arranged parallel to each other or are twisted around each other in areas where they have similar routing, before they split to separate termination points. For example, FIGS. 1 and 29 depict parallel conductive elements 210, and FIG. 40 depicts conductive elements 210 twisted around each other. The proximity of conductive elements 210 to each other, particularly if twisted around each other, may improve the quality of signals transmitted thereby. In some exemplary embodiments layers 222 and 224 may be textile or plastic material having adhesive applied to one or both sides, or may be any material or materials, such as, for example, TPU films, bonded or capable of being bonded together. In some exemplary embodiments harness 200 includes a single adhesive layer, for example, first layer 222, adhered to textile layer 100. In such an embodiment, conductive elements 210 may be positioned between first layer 222 and textile layer 100. In some exemplary embodiments, harness 200 may be screen printed on textile layer 100. For example, an insulation layer (e.g., TPU) may be screen printed on fabric layer 100 to form first layer 222, a conductive material (e.g., conductive TPU) may be screen printed on the insulation layer to form conductive elements 210, and another insulation layer may be screen printed over first layer 222 and conductive elements 210 to form second layer 224.

To produce harness 200, in some exemplary embodiments first layer 222 is laminated together with second layer 224, with conductive elements 210 positioned therebetween. In some exemplary embodiments, fabric layer 226 is laminated along with first layer 222, second layer 224, and conductive elements 210. Lamination may be accomplished by applying heat and pressure, for example by using a heat press 600, as shown in FIG. 17. Pins 610 may be inserted into a bottom plate 620 of heat press 600 at various positions, and may line up with corresponding holes in first layer 222, second layer 224, and fabric layer 226. Pins 610 may be retractable within bottom plate 620. In some exemplary embodiments, second layer 224 may be positioned on bottom plate 620 aligned with pins 610, and conductive element 210 may be laid around pins 610, using pins 610 as a guide for patterning conductive element 210 on second layer 224. First layer 222, and fabric layer 226, if provided, may then be positioned on bottom plate 620, similarly aligned with pins 610. Second layer 224, conductive element 210, first layer 222, and fabric layer 226, if provided, may then be pressed together between top plate 630 and bottom plate 620, with heat applied via either or both of top plate 630 and bottom plate 620, thereby bonding first layer 222, conductive element 210, second layer 224, and fabric layer 226, if provided, into harness 200. In some exemplary embodiments, either or both of first layer 222 and second layer 224 may include adhesive to assist bonding.

Figure 18:
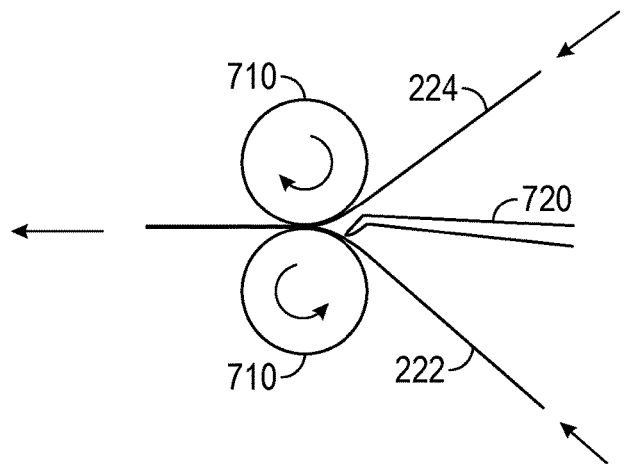
FIG. 18 is a side view of a harness manufacturing technique according to an exemplary embodiment of the present invention.
Figure 19:
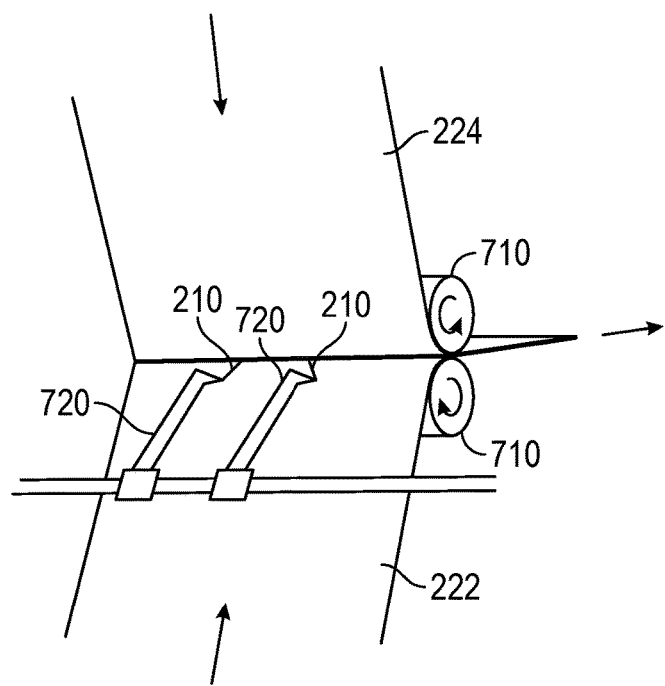
FIG. 19 is a perspective view of the harness manufacturing technique of FIG. 18 according to an exemplary embodiment of the present invention.

In some exemplary embodiments, conductive element 210 may be patterned between first layer 222 and second layer 224 via an automated process. For example, conductive element 210 may be layered on a substrate, which may be one of first layer 222 and second layer 224, and then pressed between first layer 222 and second layer 224 by rollers. In the exemplary embodiment of FIGS. 18 and 19, for example, sheets of first layer 222 and second layer 224 are shown feeding into a space between two rollers 710, which press first layer 222 and second layer 224 together to bond. In some exemplary embodiments, one or more of heat, pressure, and adhesive may be applied to assist bonding. While the layers are being fed through rollers 710, conductive element depositing heads 720 may deposit conductive element 210 in a pattern on, for example, first layer 222. Conductive element depositing heads 720 may be configured to move transversely while first layer 222 and second layer 224 are fed through rollers 710, thereby being capable of depositing conductive element 210 between first layer 222 and second layer 224 in a variety of patterns. Rollers 710 may be positioned and configured to apply appropriate heat or pressure to properly adhere first layer 222, conductive element 210, and second layer 224 together.

In some exemplary embodiments conductive element 210 may be a stretchable wire. In some exemplary embodiments, conductive element 210 may be a non-stretchable wire or conductive yarn, such as, for example, a non-stretchable conductive micro wire or conductive textile yarn, and may be twisted or wrapped around spandex or other stretchable yarn, in order to mimic elasticity.

Figure 38:
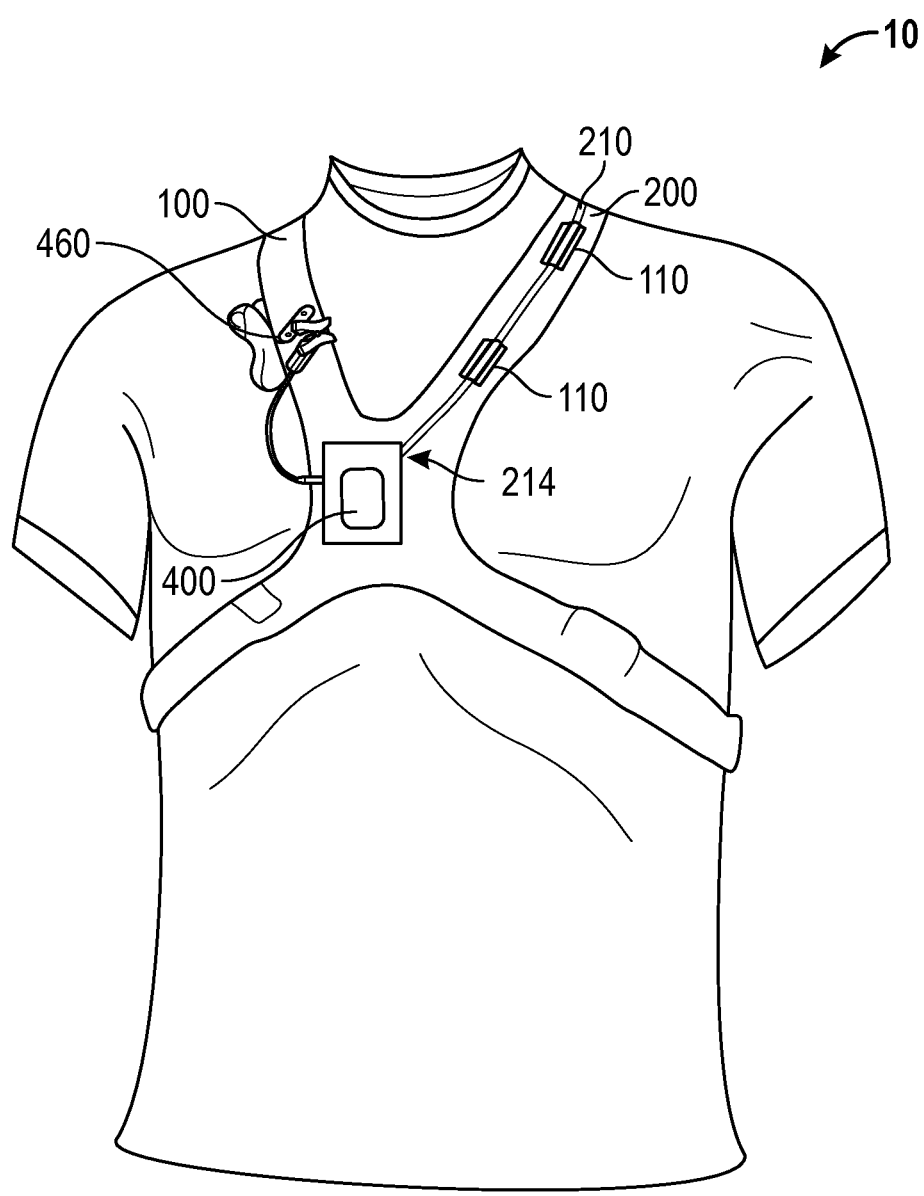
FIG. 38 is a perspective front view of a garment according to an exemplary embodiment of the present invention.
Figure 39:
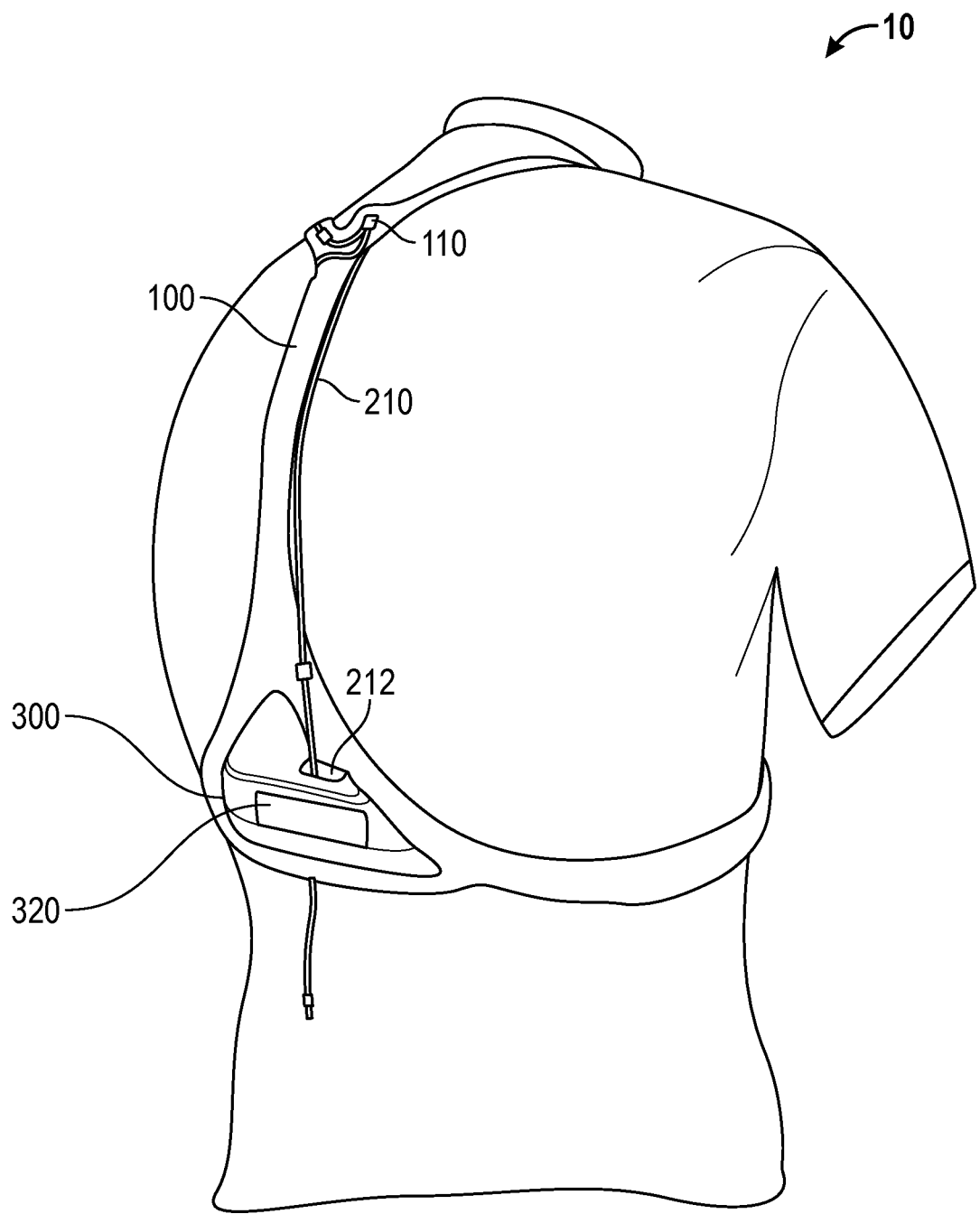
FIG. 39 is a perspective rear view of the garment of FIG. 38 according to an exemplary embodiment of the present invention.

In some exemplary embodiments, conductive element 210 may be a wire (e.g., a stretchable wire) as described above, coated with an insulating material (e.g., a stretchable insulating material). In such an embodiment, the insulating material can act as harness 200. For example, the exemplary embodiment of FIGS. 38 and 39 depicts conductive element 210 as a stretchable wire coated with a stretchable insulating material (harness 200), where the stretchable insulating material is anchored to textile layer 100 at anchor points 110. Such a configuration routes conductive elements 210 from first termination point 212, at device retention element 300 located at the back of sensor garment 10, to second termination point 214, at sensor 400 located at the chest area of sensor garment 10. Conductive element 210, coated in the stretchable insulative material, is guided to these points by being anchored to textile layer 100 at anchor points 110. In some exemplary embodiments, such as that depicted in FIG. 40, anchor points can be eliminated. In such an embodiment, conductive elements 210 may not require any particular routing, or may maintain acceptable routing by, for example, being interposed between textile layer 100 and a wearer of sensor garment 10.

In some exemplary embodiments, conductive element 210 may be a wire sewn into the seams of sensor garment 10. In some exemplary embodiments conductive element 210 may be a wire coupled to textile layer 10 at discrete points (e.g., via stitching, or adhesive), and may be otherwise free from direct connection to sensor garment. In such embodiments, harness 200 may be absent, or may simply include an insulative jacket covering conductive elements 210.

Figure 44:
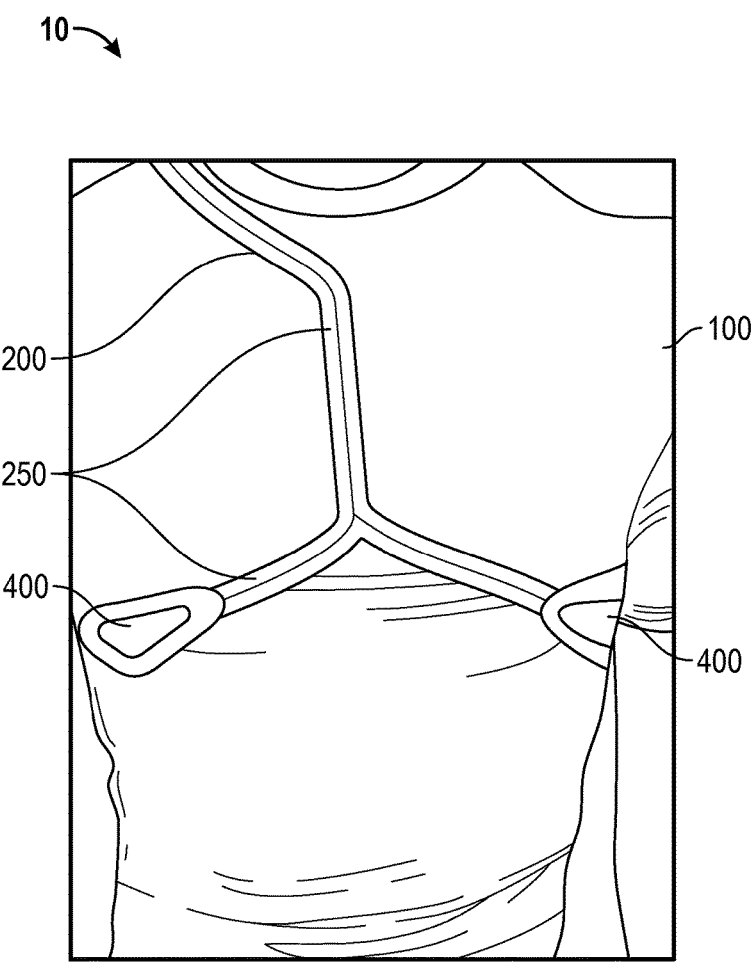
FIG. 44 is a perspective front view of a garment, shown inside-out, according to an exemplary embodiment of the present invention.

In some exemplary embodiments, harness 200 defines channels 250 coupled to or integrated within textile layer 100, through which conductive element 210 may extend, as depicted in, for example, FIG. 44, which depicts sensor garment 10 worn inside-out, for ease of description. Channels 250 may be, for example, bonded to, glued to, sewn within, connected at points to, stitched at discrete points to, ultrasonic welded to, or connected via zigzag stitch to textile layer 100. Channels 250 may be formed of fabric or other textile material, for example.

In some exemplary embodiments, conductive element 210 includes multiple termination points, corresponding with termination points of harness 200, for connection with other elements. As shown in, for example, FIGS. 3 and 4, conductive element 210 may include first termination point 212, configured to connect to monitor device 500, second termination point 214 configured to connect to a sensor 400, and third termination point 216 configured to connect to another sensor 400. In some exemplary embodiments, conductive element 210 may be configured to releasably couple with elements such as monitor device 500 or sensors 400 at a termination point. Such a connection may be established via a releasable connection element, for example, a plug, clip, snap, or latch between conductive element 210 and the element to which it is configured to releasably couple. In some exemplary embodiments, conductive element 210 may be directly connected to a component of the releasable connection element. In some exemplary embodiments, conductive element 210 may be indirectly connected to a component of the releasable connection element. For example, connection element 210 may connect directly to a conductive fabric, as described below, which may include a component of the releasable connection element.

In some exemplary embodiments, conductive element 210 may be configured to non-releasably couple with additional elements such as monitor device 500 or sensors 400. In some exemplary embodiments such a connection may be established by adhering conductive element 210 to the additional element between first layer 222 and second layer 224 via, for example, a heated or ultrasonic weld. In some exemplary embodiments such a connection may be established by a conductive gel (e.g., conductive epoxy, silicone with conductive particles (e.g., silver, carbon, or stainless steel)) applied between conductive element 210 and the additional element. In some exemplary embodiments such a connection may be established by a conductive fabric.

In some exemplary embodiments, a conductive fabric connection 410 between conductive element 210 and a sensor 400 includes conductive adhesive 412 and conductive fabric 414 (see FIG. 16). In such a connection, conductive fabric 414 acts as a bridge between conductive element 210 and sensor 400. Conductive fabric 414 connects to conductive element 210 via, for example, stitching, adhesive film, conductive epoxy, or conductive adhesive 412, and to sensor 400 via, for example, adhesive, stitching, or conductive epoxy. Conductive fabric 414 may be, for example, a metal woven mesh, a stretchable conductive fiber, a rigid conductive mesh, a conductive foil, or a conductive polymer. Conductive fabric 414 can be any suitable size and shape, including, for example, sized and/or shaped to correspond to the head of a snap used to establish connection to monitor device 500, or sized and/or shaped to correspond to the amount of conductive adhesive 412 used to establish connection to conductive element 210. In some exemplary embodiments, where conductive elements 210 are conductive yarn, the conductive yarn can be used as sewing thread to connect to conductive fabric 414.

The present invention has been described above by way of exemplary embodiments. Accordingly, the present invention should not be limited by any of the above-described exemplary embodiments, but should be defined only in accordance with the following claims and their equivalences.

What is claimed is:

1. A garment comprising:
   a textile layer;
   a sensor coupled to the textile layer; and
   an electrically conductive element coupled to the sensor and configured to transmit data from the sensor,
   wherein the electrically conductive element is arranged in a pattern and comprises a first section having a first repeating pattern and a second section having a second repeating pattern, the second repeating pattern being different than the first repeating pattern in at least one of frequency or magnitude, and
   wherein the second section is configured to be more flexible than the first section.

2. The garment of claim 1, wherein the electrically conductive element is wire.

3. The garment of claim 1, wherein the electrically conductive element is non-stretchable wire.

4. The garment of claim 1, wherein the pattern is at least one of a sinusoidal pattern, a zig-zag pattern, or a looping pattern.

5. The garment of claim 1, wherein the sensor comprises a resistance sensor.

6. The garment of claim 5,
   wherein the resistance sensor senses deformation of the electrically conductive element by sensing variation in resistance of the electrically conductive element.

7. The garment of claim 1, wherein the electrically conductive element is coupled to the textile layer.

8. The garment of claim 1, further comprising a harness comprising the electrically conductive element.

9. The garment of claim 1, further comprising a harness comprising the electrically conductive element,
   wherein the harness comprises a layer coupled to the textile layer, and
   wherein the electrically conductive element is disposed between the layer and the textile layer.

10. The garment of claim 1, wherein the electrically conductive element adopts a greater frequency closer to an endpoint of the electrically conductive element.

11. The garment of claim 1, wherein the electrically conductive element adopts a lesser magnitude closer to an endpoint of the electrically conductive element.

12. The garment of claim 1, wherein the second repeating pattern is different from the first repeating pattern in frequency.

13. The garment of claim 1, wherein the second repeating pattern is different from the first repeating pattern in magnitude.

14. The garment of claim 1, wherein the second repeating pattern is different from the first repeating pattern in both frequency and magnitude.

15. A garment comprising:
   a textile layer having a flexible textile portion and a less flexible textile portion;
   a sensor coupled to the textile layer; and
   an electrically conductive element coupled to the sensor and configured to transmit data from the sensor, the electrically conductive element being flexible and having a first length and a second length,
   wherein the first length extends over the flexible textile portion and is fixed relative to the flexible textile portion, and
   wherein the second length extends over the less flexible textile portion and is not fixed relative to the less flexible textile portion.

16. The garment of claim 15, further comprising a harness comprising the electrically conductive element, wherein the harness has a first length and a second length,
   wherein the first length of the electrically conductive element is disposed along the first length of the harness,
   wherein the second length of the electrically conductive element is disposed along the second length of the harness,
   wherein the first length of the harness extends over the flexible textile portion and is fixed relative to the flexible textile portion, and
   wherein the second length of the harness extends over the less flexible textile portion and is not fixed relative to the less flexible textile portion.

17. The garment of claim 15, wherein the flexible textile portion extends from a back to a front of the garment, and
   wherein the less flexible textile portion extends across the front of the garment.

18. A garment comprising:
   a textile layer forming a shape of the garment and having a flexible textile portion and a less flexible textile portion; and
   a harness coupled to the textile layer, the harness comprising an electrically conductive element and extending from a back of the garment, over a shoulder of the garment to a front of the garment, and splitting at the front of the garment to extend to a right side of the front of the garment and a left side of the front of the garment,
   wherein a first portion of the harness extends over and is fixed relative to the flexible textile portion and wherein a second portion of the harness extends over and is not fixed relative to the less flexible textile portion.

19. The garment of claim 18, further comprising a device-retention element, wherein the harness terminates at the back of the garment at the device-retention element.

20. The garment of claim 18, further comprising:
   a first sensor; and
   a second sensor,
   wherein the harness terminates at the front of the garment at the first sensor and at the second sensor.

21. The garment of claim 18, further comprising:
   a back electronic element disposed at the back of the garment; and
   two front electronic elements disposed at the front of the garment and spaced apart from each other,
   wherein the harness electrically connects the back electronic element to the two front electronic elements.

22. The garment of claim 21, wherein the front electronic elements are physiological sensors, and
   wherein the back electronic element is a monitor device that receives signals from the physiological sensors via the harness and transmits the signals to a remote device.

23. The garment of claim 21, wherein the harness extends over only one shoulder of the garment.

24. The garment of claim 18, wherein the electrically conductive element comprises at least a first electrically conductive element and a second electrically conductive element, the first and second electrically conductive elements extending together up to where the harness splits at the front of the garment, and extending separately thereafter, wherein the first and second electrically conductive elements are parallel to each other or twisted around each other where they extend together.

\* \* \* \* \*